United States Patent
Takimiya et al.

(10) Patent No.: US 9,859,508 B2
(45) Date of Patent: Jan. 2, 2018

(54) CONDENSED POLYCYCLIC AROMATIC COMPOUND AND USE THEREOF

(71) Applicant: Nippon Kayaku Kabushiki Kaisha, Tokyo (JP)

(72) Inventors: Kazuo Takimiya, Saitama (JP); Shoji Shinamura, Tokyo (JP); Masahiro Hamada, Tokyo (JP); Yuichi Sadamitsu, Tokyo (JP)

(73) Assignee: Nippon Kayaku Kabushiki Kaisha, Tokyo (JP)

(*) Notice: Subject to any disclaimer, the term of this patent is extended or adjusted under 35 U.S.C. 154(b) by 151 days.

(21) Appl. No.: 14/771,213

(22) PCT Filed: Feb. 27, 2014

(86) PCT No.: PCT/JP2014/054937
§ 371 (c)(1),
(2) Date: Aug. 28, 2015

(87) PCT Pub. No.: WO2014/133100
PCT Pub. Date: Sep. 4, 2014

(65) Prior Publication Data
US 2016/0013428 A1    Jan. 14, 2016

(30) Foreign Application Priority Data
Feb. 28, 2013  (JP) ................ 2013-038582

(51) Int. Cl.
*H01L 51/00*  (2006.01)
*C07D 495/04*  (2006.01)
(Continued)

(52) U.S. Cl.
CPC ........ *H01L 51/0074* (2013.01); *C07D 493/04* (2013.01); *C07D 495/04* (2013.01);
(Continued)

(58) Field of Classification Search
None
See application file for complete search history.

(56) References Cited

U.S. PATENT DOCUMENTS

| | | |
|---|---|---|
| 2011/0224445 A1 | 9/2011 | Takimiya |
| 2012/0001158 A1* | 1/2012 | Asari ................ C07D 487/04 257/40 |

FOREIGN PATENT DOCUMENTS

| | | |
|---|---|---|
| CA | 2298800 A1 | 8/2000 |
| CN | 101693719 A | 4/2010 |

(Continued)

OTHER PUBLICATIONS

Machine English translation of Takimiya (CN 102224157 A). Aug. 22, 2017.*

(Continued)

*Primary Examiner* — J. L. Yang
(74) *Attorney, Agent, or Firm* — Nields, Lemack & Frame, LLC

(57) ABSTRACT

[Problem] To provide: a novel compound which has high mobility and on/off ratio and is useful for organic electronic devices; and a method for producing the compound.
[Solution] A condensed polycyclic aromatic compound which is represented by general formula (1). (In the formula, A represents a 1,5-dihydronaphthalene ring or a 2,6-dihydronaphthalene ring; each of $R_1$, $R_2$, $R_3$ and $R_4$ independently represents a hydrogen atom, a halogen atom, a substituted or unsubstituted aliphatic hydrocarbon group, a substituted or unsubstituted alicyclic hydrocarbon group, a substituted or unsubstituted aromatic hydrocarbon group, a substituted or unsubstituted hydrocarbon oxy group, a substituted or unsubstituted ester group, a substituted or unsubstituted acyl group, or a substituted or unsubstituted cyano (Continued)

group; and each of $X_1$ and $X_2$ independently represents an oxygen atom, a sulfur atom or a selenium atom.)

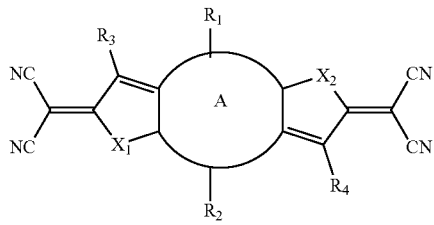

(1)

14 Claims, 3 Drawing Sheets

(51) Int. Cl.
C07D 493/04 (2006.01)
C07D 517/04 (2006.01)
H01L 51/05 (2006.01)

(52) U.S. Cl.
CPC ........ *C07D 517/04* (2013.01); *H01L 51/0051* (2013.01); *H01L 51/0541* (2013.01); *H01L 51/0545* (2013.01); *H01L 51/0558* (2013.01)

(56) References Cited

FOREIGN PATENT DOCUMENTS

| CN | 102224157 A | * | 10/2011 |
| EP | 2068379 A1 | | 6/2009 |
| JP | 2009242339 A | | 10/2009 |
| WO | 2008032715 A1 | | 3/2008 |

OTHER PUBLICATIONS

Chinese communication, with English translation, dated May 4, 2016 in corresponding Chinese patent application No. 201480011277.2.
Pappenfus et al, Journal of the American Chemical Society, 2002, 124, p. 4184-4185.
Kashiki, T. et al, Chemistry Letters, 2009, vol. 38, No. 6, p. 568-569, Fig. 1.
Mori, T. et al, Organic Letters, Feb. 24, 2014, vol. 16, p. 1334-1337, Scheme 1.
Shu Yoshida, et al, Journal of Organic Chemistry, 1994, 59 (11), p. 3077-3081.
Shoji Shinamura et al, Organic Letters, vol. 14, No. 18, Sep. 12, 2012, p. 4718-4721.
Dawei Yue et al, Journal of Organic Chemistry, 2005, 70 (25), p. 10292-10296.
Dawei Yue et al, Journal of Organic Chemistry, 2002, 67 (6), p. 1905-1909.
Ibraheem A. I. Mkhalid et al, Chemical Reviews, 2010, 110 (2), p. 890-931.
International Preliminary Report on Patentability dated Sep. 1, 2015 in corresponding PCT application No. PCT/JP2014/054937.
International Search Report and Written Opinion dated Apr. 15, 2014 in corresponding PCT application No. PCT/JP2014/054937.
Chinese communication, with English translation, dated Dec. 19, 2016 in corresponding Chinese patent application No. 01480011277.2.
Taiwanese communication, with English translation, dated May 23, 2017 in corresponding Taiwanese patent application No. 103106750.

* cited by examiner

CONDENSED POLYCYCLIC AROMATIC COMPOUND AND USE THEREOF

TECHNICAL FIELD

The present invention relates to a condensed polycyclic aromatic compound, an organic semiconductor material and organic semiconductor device comprising the same, and methods for manufacturing a condensed polycyclic aromatic compound and an organic semiconductor device. More specifically, the present invention relates to a condensed polycyclic aromatic compound that allows a transistor to stably operate even in the air atmosphere, an organic semiconductor material and organic semiconductor device comprising the same, and methods for producing the condensed polycyclic aromatic compound and organic semiconductor device.

BACKGROUND ART

In recent years, thin film devices containing organic semiconductor materials, such as organic EL devices, organic transistor devices and organic thin film photoelectric conversion devices, have attracted attention and have started to be put in practical use. Among the fundamental physical properties of organic semiconductor materials to be used for these thin film devices, carrier mobility and on/off ratio are important. For example, in organic EL devices, efficient charge transport is required for highly efficient luminescence and driving at a low voltage, and carrier mobility is thus important. In organic transistor devices, carrier mobility and on/off ratio, which directly affect their switching speeds and the performance of a device to be driven, are also important.

Further, it is important that they can be stably driven in the air atmosphere. If stably driven in the air atmosphere, it would make work or operation in an inert atmosphere and sealing or the like unnecessary. Hence, the production processes can be simplified and the cost of equipment necessary for the production can be greatly reduced.

In organic semiconductor materials, as with inorganic semiconductor materials, known conventionally are p-type (hole transport) organic semiconductor materials (hereinafter, referred to as "p-type materials") and n-type (electron transport) organic semiconductor materials (hereinafter, referred to as "n-type materials"). For example, in order to fabricate a logical circuit such as a CMOS (complementary metal oxide semiconductor), a p-type material and an n-type material have been required.

Many studies on p-type materials have been made so far, and materials which exhibit high performance and are stably driven in the air atmosphere have been reported. In contrast, studies on n-type materials have not so much progressed. Many of the materials which have recently been developed, can be driven only in vacuum, and those capable of being driven stably in the air atmosphere are limited.

Compounds having a quinoid structure are a kind of n-type materials capable of being driven stably in the air atmosphere, and quinoid oligothiophene, quinoid benzodithiophene and the like have been developed (Patent Literatures 1 and 2, and Non Patent Literatures 1 and 2). However, it cannot be said that these compounds have sufficient performance, and the they have not put into commercial use. Therefore, there is a need for a semiconductor material having high mobility and a high on/off ratio.

CITATION LIST

Patent Literature

Patent Literature 1: WO2008-032715
Patent Literature 2: JP 2009-242339 A

Non Patent Literature

Non Patent Literature 1: J. Am. Chem. Soc., 2002, 124, 4184
Non Patent Literature 2: Chem. Lett., 2009, vol.38, 568

SUMMARY OF INVENTION

Technical Problem

An object of the present invention is to provide an n-type semiconductor material being stable in the air atmosphere and having high mobility and a large on/off ratio.

Solution to Problem

In order to solve the above-mentioned problems, the present inventors have developed a novel condensed polycyclic aromatic compound, and further have studied the potential thereof for use in an organic electric device, thereby completing the present invention.

That is, the present invention relates to the following.

[1] A condensed polycyclic aromatic compound represented by general formula (1):

[Formula 1]

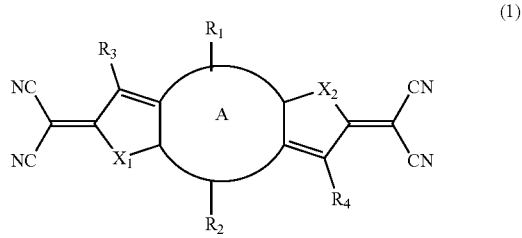

(1)

wherein A represents a 1,5-dihydronaphthalene ring or a 2,6-dihydronaphthalene ring; $R_1$, $R_2$, $R_3$ and $R_4$ each independently represent a hydrogen atom, a halogen atom, a substituted or unsubstituted aliphatic hydrocarbon group, a substituted or unsubstituted alicyclic hydrocarbon group, a substituted or unsubstituted aromatic hydrocarbon group, a substituted or unsubstituted hydrocarbon oxy group, a substituted or unsubstituted ester group, a substituted or unsubstituted acyl group or a substituted or unsubstituted cyano group; and $X_1$ and $X_2$ each independently represent an oxygen atom, a sulfur atom or a selenium atom.

[2] The condensed polycyclic aromatic compound according to [1], wherein $X_1$ and $X_2$ are sulfur atoms.

[3] The condensed polycyclic aromatic compound according to [1] or [2], wherein $R_3$ and $R_4$ are a hydrogen atom.

[4] The condensed polycyclic aromatic compound according to any one of [1] to [3], wherein $R_1$ and $R_2$ are an aliphatic hydrocarbon group having 1 to 30 carbon atoms.

[5] The condensed polycyclic aromatic compound according to [4], wherein $R_1$ and $R_2$ are a straight-chain or branched-chain alkyl group having 1 to 30 carbon atoms.

[6] An organic semiconductor material comprising the condensed polycyclic aromatic compound according to any one of [1] to [5].
[7] The organic semiconductor material according to [6], wherein the organic semiconductor material is a transistor material.
[8] A composition for forming a thin film comprising the condensed polycyclic aromatic compound according to any one of [1] to [5], and an organic solvent.
[9] The composition for forming a thin film according to [8], wherein the content of the condensed polycyclic aromatic compound is in the range of 0.01 part by weight or higher and 10 parts by weight or lower relative to 100 parts by weight of the solvent.
[10] A thin film comprising a condensed ring aromatic compound according to any one of [1] to [5].
[11] An organic semiconductor device comprising the thin film according to [10].
[12] The organic semiconductor device according to [11], wherein the device is an organic transistor device.
[13] A method for producing an organic semiconductor device, comprising a step of applying the composition for forming a thin film according to [8] or [9] onto a substrate by a solution process.

Advantageous Effects of Invention

The present invention relates to a novel condensed polycyclic aromatic compound, which is an n-type semiconductor capable of being stably driven in the air atmosphere and has high mobility and a great on/off ratio. The compound can be thus used to provide an organic electro-device.

DESCRIPTION OF EMBODIMENTS

Figure 1:
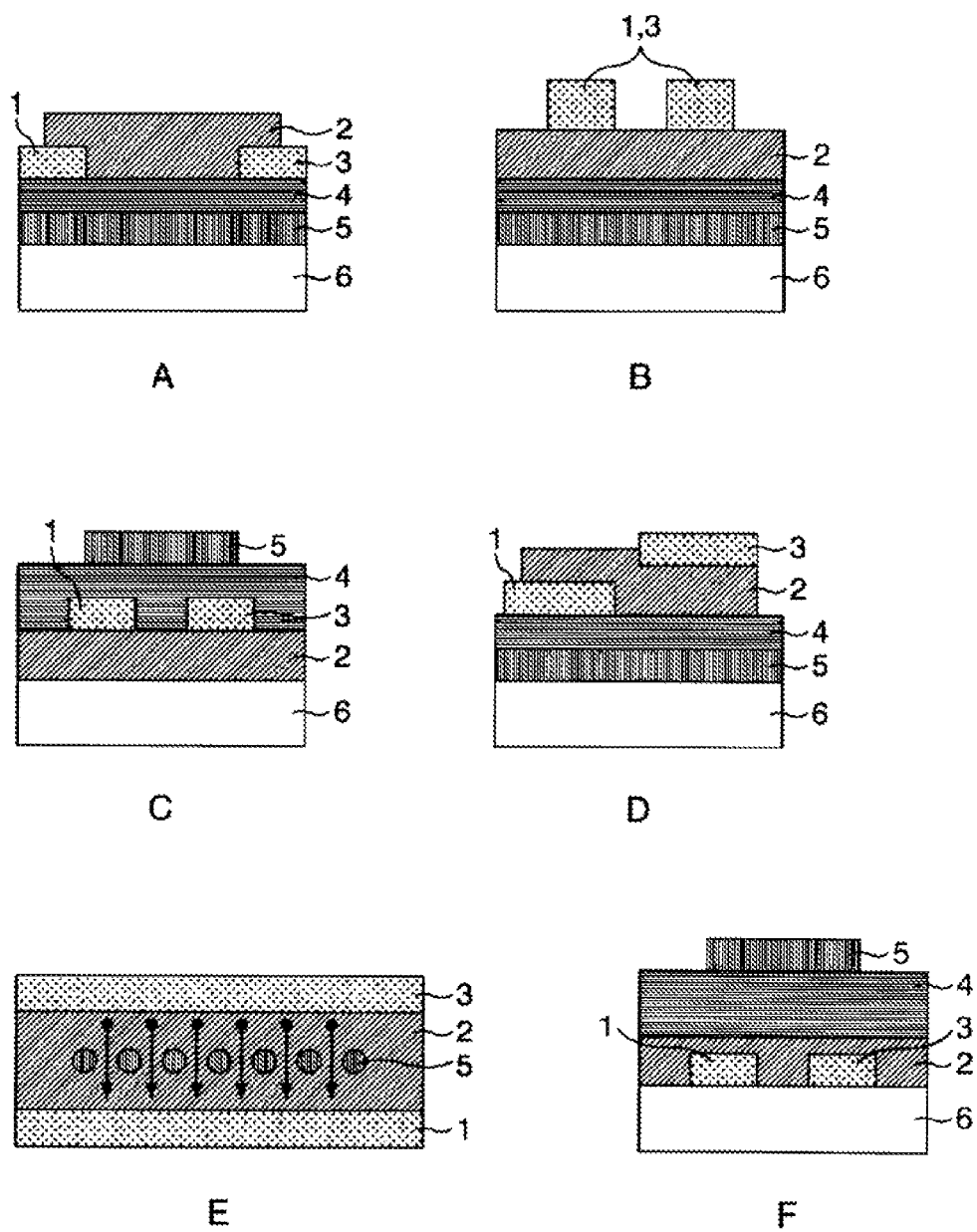
FIG. 1 is schematic views illustrating the structures of organic transistors according to embodiments of the present invention.

The present invention will be described in detail hereinafter.
A condensed polycyclic aromatic compound represented by the following general formula (1) will be described.

[Formula 4]

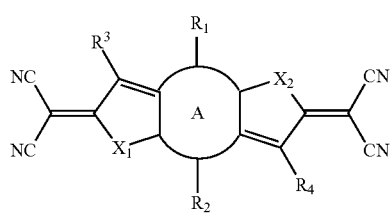

(1)

In general formula (1), A represents a 1,5-dihydronaphthalene ring or a 2,6-dihydronaphthalene ring. $R_1$ to $R_4$ each independently represent a hydrogen atom, a halogen atom, an aliphatic hydrocarbon group, an alicyclic hydrocarbon group, an aromatic hydrocarbon group, a hydrocarbon oxy group, an ester group, an acyl group or a cyano group, wherein the aliphatic hydrocarbon group, the alicyclic hydrocarbon group, the aromatic hydrocarbon group, the hydrocarbon oxy group, the ester group, the acyl group, and the cyano group may be substituted or unsubstituted. The position, the number and the type of a substituent are not particularly limited; and in the case of having two or more substituents, two or more kinds of substituents can be concurrently present. The substituent may be a halogen atom, an aliphatic hydrocarbon group, an alicyclic hydrocarbon group, an aromatic hydrocarbon group, a hydrocarbon oxy group, an ester group, an acyl group or a cyano group. $X_1$ and $X_2$ each independently represent an oxygen atom, a sulfur atom or a selenium atom.

Preferably, $R_1$ to $R_4$ are all a hydrogen atom; or $R_1$ and $R_2$ are a hydrogen atom, and $R_3$ and $R_4$ are each an aliphatic hydrocarbon group or an aromatic hydrocarbon group; or $R_1$ and $R_2$ are each a halogen atom, an aliphatic hydrocarbon group, an alicyclic hydrocarbon group, an aromatic hydrocarbon group, a hydrocarbon oxy group, an ester group, an acyl group or a cyano group, and $R_3$ and $R_4$ are a hydrogen atom. More preferably, $R_1$ and $R_2$ are each an aliphatic hydrocarbon group, and $R_3$ and $R_4$ are a hydrogen atom. $X_1$ and $X_2$ are preferably a sulfur atom.

The halogen atom includes a fluorine atom, a chlorine atom, a bromine atom and an iodine atom.
The aliphatic hydrocarbon group includes a saturated or unsaturated straight-chain or branched-chain aliphatic hydrocarbon group; and the number of carbon atoms thereof is preferably 1 to 30, more preferably 1 to 20, and still more preferably 6 to 18. Examples of the saturated or unsaturated straight-chain or branched-chain alkyl group include a methyl group, an ethyl group, a propyl group, an isopropyl group, a n-butyl group, an isobutyl group, an allyl group, a t-butyl group, a n-pentyl group, a n-hexyl group, a n-octyl group, a n-decyl group, a n-dodecyl group, a n-tridecyl group, a n-tetradecyl group, a n-cetyl group, a n-heptadecyl group, a n-butenyl group, a 2-ethylhexyl group, a 3-ethylheptyl group, a 4-ethyloctyl group, a 2-butyloctyl group, a 3-butylnonyl group, a 4-butyldecyl group, a 2-hexyldecyl group, a 3-octylundecyl group, a 4-octyldodecyl group, a 2-octyldodecyl group and a 2-decyltetradecyl group. The aliphatic hydrocarbon group may be preferably a saturated straight-chain or branched-chain alkyl group and especially preferably a n-octyl group, a n-decyl group, a n-dodecyl group, a n-cetyl group, a 2-ethylhexyl group, a 2-butyloctyl group, a 2-hexyldecyl group or a 4-ethyloctyl group.

The alicyclic hydrocarbon group includes a saturated or unsaturated cyclic hydrocarbon group; and examples of the cyclic hydrocarbon group include a cyclic hydrocarbon group having 3 to 12 carbon atoms such as a cyclohexyl group, a cyclopentyl group, an adamantyl group and a norbornyl group.

The aromatic hydrocarbon group includes a phenyl group, a naphthyl group, an anthryl group, a phenanthryl group, a pyrenyl group and a benzopyrenyl group. Among these, preferable are a phenyl group and a naphthyl group; and especially preferable is a phenyl group.

The heterocyclic group or the condensed heterocyclic group includes a pyridyl group, a pyrazyl group, a pyrimidyl group, a quinolyl group, an isoquinolyl group, a pyrrolyl group, an indolenyl group, an imidazolyl group, a carbazolyl group, a thienyl group, a furyl group, a pyranyl group, a pyridonyl group, a benzoquinolyl group, an anthraquinolyl group, a benzothienyl group and a benzofuryl group. Among these, preferable are a pyridyl group and a thienyl group; and especially preferable is a thienyl group.

The hydrocarbon oxy group includes a hydrocarbon oxy group containing any of the above-mentioned aliphatic hydrocarbon groups.

The ester group and the acyl group include an ester group containing any of the above-mentioned aliphatic hydrocarbon groups and an acyl group containing any of the above-mentioned aliphatic hydrocarbon groups.

Preferable combinations of $R_1$ to $R_4$, and $X_1$ and $X_2$ in formula (1) are combinations of the preferable groups or atoms described above.

A condensed polycyclic aromatic compound of general formula (1) can be obtained by a reaction of a compound of general formula (2) with a compound of general formula (3) as in the following scheme.

[Formula 5]

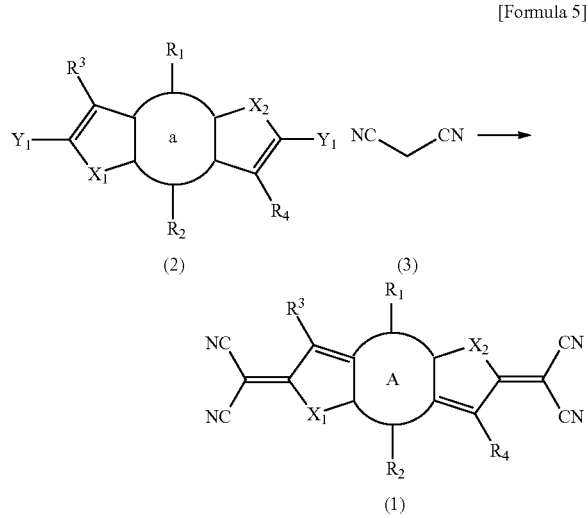

In general formula (2), $X_1$ and $X_2$ each independently represent an oxygen atom, a sulfur atom or a selenium atom. a represents a naphthalene ring. $R_1$ to $R_4$ each independently represent a hydrogen atom, a halogen atom, an aliphatic hydrocarbon group, an alicyclic hydrocarbon group, an aromatic hydrocarbon group, a hydrocarbon oxy group, an ester group, an acyl group or a cyano group, wherein the aliphatic hydrocarbon group, the alicyclic hydrocarbon group, the aromatic hydrocarbon group, the hydrocarbon oxy group, the ester group, the acyl group, and the cyano group may be substituted or unsubstituted. The position, the number and the type of a substitute are not especially limited; and in the case of having two or more substituents, two or more kinds of substituents can be concurrently present. The substituent may be a halogen atom, an aliphatic hydrocarbon group, an alicyclic hydrocarbon group, an aromatic hydrocarbon group, a hydrocarbon oxy group, an ester group, an acyl group or a cyano group. The aliphatic hydrocarbon group, the alicyclic hydrocarbon group, the aromatic hydrocarbon group, the hydrocarbon oxy group, the ester group, the acyl group, and the cyano group are as mentioned as to $R_1$ to $R_4$. $Y_1$ represents a halogen atom; and the halogen atom includes a fluorine atom, a chlorine atom, a bromine atom and an iodine atom. Preferable are a bromine atom and an iodine atom.

Preferable combinations of $R_1$ to $R_4$ and $X_1$ and $X_2$ in formula (2) are the same as the preferable combinations mentioned as to $R_1$ to $R_4$, and $X_1$ and $X_2$ in formula (1).

A condensed polycyclic aromatic compound represented by general formula (1) according to the present invention can be synthesized by, for example, applying a method described in J. Org. Chem., 1994, 59, 3077. Specifically, a condensed polycyclic aromatic compound of general formula (1) can be obtained by reacting a compound of general formula (2) with a compound of general formula (3) in a solvent or no solvent in the presence of a catalyst and a base.

The catalyst to be used in the reaction preferably includes a palladium-based catalyst such as $PdCl_2(PPh_3)_2$, $Pd(PPh_3)_4$, $Pd(OAc)_2$ and $PdCl_2$. The amount of the catalyst is not especially limited, but is 0.001 to 1 mol, preferably 0.01 to 0.5 mol, and more preferably 0.05 mol to 0.3 mol per mol of a compound of general formula (2). There may also be used, for example, a phosphine-based ligand such as triphenylphosphine, 1,1'-bis(diphenylphosphino)ferrocene (dppf), 1,2-bis(diphenylphosphino)ethane (dppe) or 1,3-bis(diphenylphosphino)propane (dppp).

The base includes inorganic bases such as potassium carbonate, sodium carbonate, potassium hydride and sodium hydride, and preferably includes sodium hydride. The amount of the base is not especially limited as long as it is sufficient for the reaction, but is 0.1 to 100 mol, preferably 0.5 to 50 mol, and more preferably 1 to 10 mol per mol of a compound of general formula (2).

The reaction may be carried out without a solvent, but can be preferably carried out with a solvent, which includes, for example, an ether such as diethyl ether, anisole and tetrahydrofuran; an amide such as dimethylacetamide and dimethylformamide; a nitrile such as acetonitrile, propionitrile and benzonitrile; and an alcohol such as methanol, ethanol and butanol. The solvent is preferably an ether such as tetrahydrofuran. The amount of the solvent is not especially limited, but may be about 0 to 10,000 mol per mol of a compound of general formula (2).

The reaction temperature may be in the range of −50° C. to 300° C. The reaction temperature can vary within this range, but is more preferably 0° C. to 250° C. and still more preferably 10° C. to 200° C. In general, the reaction may be preferably completed in a short time. The reaction time at this time may be preferably 10 min to 1,000 hours, more preferably 30 min to 100 hours, and still more preferably 30 min to 24 hours. The reaction temperature, and the amounts of a catalyst, a base and a solvent can be adjusted so as to complete the reaction in a short time.

As requested, a substance of interest may be isolated and purified from the reaction mixture by a known isolating or purifying method. In the case of using a substance as an organic semiconductor material, high purity is required in many cases; and such high purity compounds can be obtained by a known method such as recrystallization, column chromatography and vacuum sublimation purification. These methods may be conducted in combination as required.

A compound represented by general formula (2) can be produced by a well-known method.

For instance, a compound represented by general formula (2) can be produced by halogenation of a compound represented by general formula (4) in accordance with Chem. Rev., 2010, 110, 890.

[Formula 6]

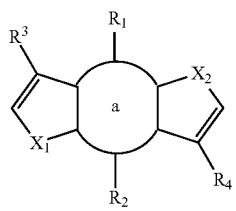

(4)

A compound represented by general formula (4) can be synthesized by a method described in Org. Lett., 2012, 14, 4718.

a, $X_1$ and $X_2$, and $R_1$ to $R_4$ in general formula (4) are the same as described above.

Specific exemplary condensed polycyclic aromatic compounds represented by the general formula (1) are described below. Table 1 shows compounds represented by general formula (5). The present invention is not to be limited thereto.

[Formula 7]

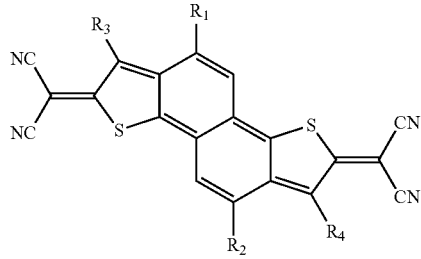

(5)

TABLE 1

|     | R1 | R2 | R3 | R4 |
|-----|----|----|----|----|
| 101 | H | H | H | H |
| 102 | CH$_3$ | H | H | H |
| 103 | C$_2$H$_5$ | C$_2$H$_5$ | H | H |
| 104 | n-C$_3$H$_7$ | n-C$_3$H$_7$ | H | H |
| 105 | iso-C$_3$H$_7$ | iso-C$_3$H$_7$ | H | H |
| 106 | n-C$_4$H$_9$ | n-C$_4$H$_9$ | H | H |
| 107 | iso-C$_4$H$_9$ | iso-C$_4$H$_9$ | H | H |
| 108 | tert-C$_4$H$_9$ | tert-C$_4$H$_9$ | H | H |
| 109 | n-C$_6$H$_{13}$ | n-C$_6$H$_{13}$ | H | H |
| 110 | n-C$_8$H$_{17}$ | n-C$_8$H$_{17}$ | H | H |
| 111 | n-C$_{10}$H$_{21}$ | n-C$_{10}$H$_{21}$ | H | H |
| 112 | n-C$_{12}$H$_{25}$ | n-C$_{12}$H$_{25}$ | H | H |
| 113 | n-C$_{14}$H$_{29}$ | n-C$_{14}$H$_{29}$ | H | H |
| 114 | n-C$_{16}$H$_{33}$ | n-C$_{16}$H$_{33}$ | H | H |
| 115 | n-C$_{18}$H$_{37}$ | n-C$_{18}$H$_{37}$ | H | H |
| 116 | n-C$_{20}$H$_{41}$ | n-C$_{20}$H$_{41}$ | H | H |
| 117 | cyclohexyl | cyclohexyl | H | H |
| 118 | cyclopentyl | cyclopentyl | H | H |
| 119 | -CH$_2$CH(C$_2$H$_5$)C$_4$H$_9$ | -CH$_2$CH(C$_2$H$_5$)C$_4$H$_9$ | H | H |
| 120 | -CH$_2$CH(C$_4$H$_9$)C$_6$H$_{13}$ | -CH$_2$CH(C$_4$H$_9$)C$_6$H$_{13}$ | H | H |
| 121 | -CH$_2$CH(C$_6$H$_{13}$)C$_8$H$_{17}$ | -CH$_2$CH(C$_6$H$_{13}$)C$_8$H$_{17}$ | H | H |
| 122 | -CH$_2$CH(C$_8$H$_{17}$)C$_{10}$H$_{21}$ | -CH$_2$CH(C$_8$H$_{17}$)C$_{10}$H$_{21}$ | H | H |

TABLE 1-continued
| | R1 | R2 | R3 | R4 |
|---|---|---|---|---|
| 123 | 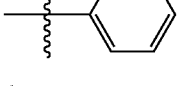 | 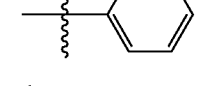 | H | H |
| 124 | 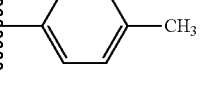 | 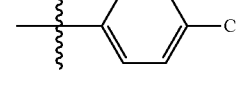 | H | H |
| 125 | 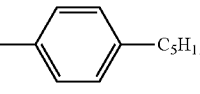 | 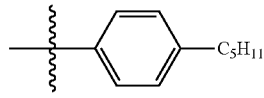 | H | H |
| 126 | 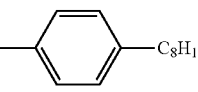 | 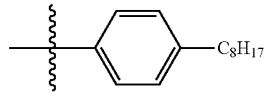 | H | H |
| 127 | 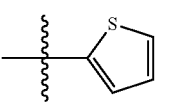 [SMILES: *c1cccs1] | 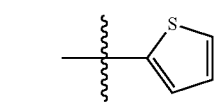 | H | H |
| 128 | 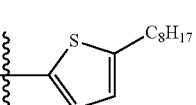 | 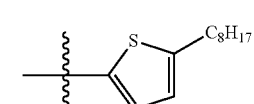 | H | H |
| 129 | 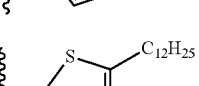 | 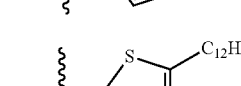 | H | H |
| 130 |  |  | H | H |
| 131 | 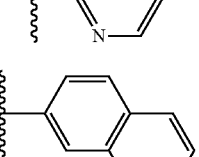 | 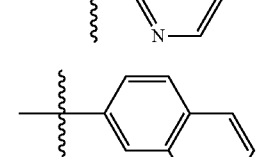 | H | H |
| 132 | 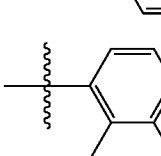 | 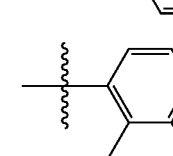 | H | H |
| 133 | 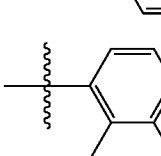 | 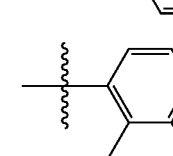 | H | H |
| 134 | $OCH_3$ | $OCH_3$ | H | H |
| 135 | $OC_8H_{17}$ | $OC_8H_{17}$ | H | H |
| 136 | $OC_{12}H_{25}$ | $OC_{12}H_{25}$ | H | H |
| 137 | $CO_2CH_3$ | $CO_2CH_3$ | H | H |
| 138 | $CO_2C_8H_{17}$ | $CO_2C_8H_{17}$ | H | H |
| 139 | $CO_2C_{12}H_{25}$ | $CO_2C_{12}H_{25}$ | H | H |
| 140 | $COCH_3$ | $COCH_3$ | H | H |
| 141 | $COC_8H_{17}$ | $COC_8H_{17}$ | H | H |
| 142 | $COC_{12}H_{25}$ | $COC_{12}H_{25}$ | H | H |
| 143 | CN | CN | H | H |
| 144 | F | F | H | H |
| 145 | Cl | Cl | H | H |
| 146 | H | H | $n\text{-}C_8H_{17}$ | $n\text{-}C_8H_{17}$ |

TABLE 1-continued
| | R1 | R2 | R3 | R4 |
|---|---|---|---|---|
| 147 | n-C$_8$H$_{17}$ | n-C$_8$H$_{17}$ | n-C$_8$H$_{17}$ | n-C$_8$H$_{17}$ |
| 148 | H | H | phenyl | phenyl |
| 149 | phenyl | phenyl | phenyl | phenyl |
| 150 | phenyl | n-C$_8$H$_{17}$ | H | H |
| 151 | 4-C$_5$H$_{11}$-phenyl | n-C$_8$H$_{17}$ | H | H |
[Formula 8]
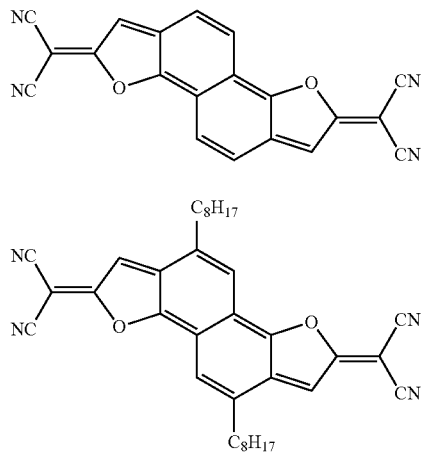
152
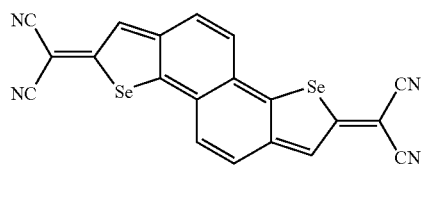
153
[Formula 9]
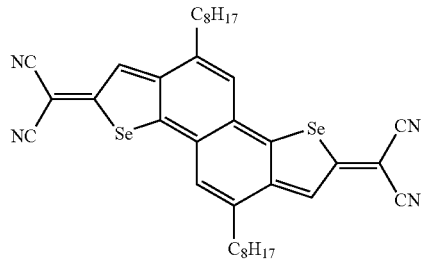
154
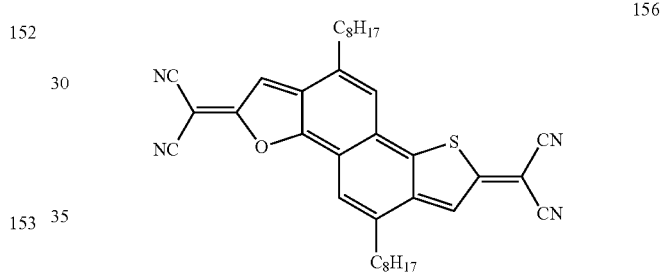
155
[Formula 10]
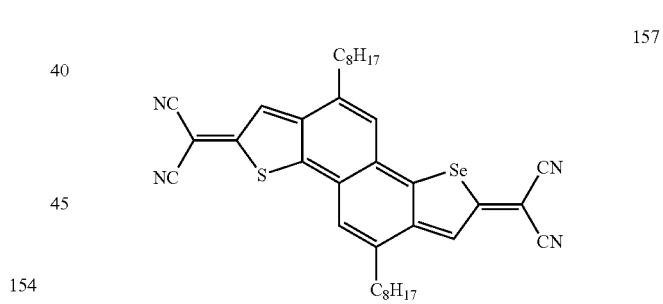
156
157
Table 2 shows compounds represented by general formula (6). The present invention is not to be limited thereto.
[Formula 11]
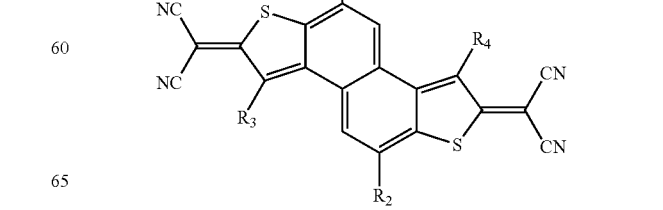
(6)

TABLE 2
| | R₁ | R₂ | R₃ | R₄ |
|---|---|---|---|---|
| 201 | H | H | H | H |
| 202 | CH₃ | H | H | H |
| 203 | C₂H₅ | C₂H₅ | H | H |
| 204 | n-C₃H₇ | n-C₃H₇ | H | H |
| 205 | iso-C₃H₇ | iso-C₃H₇ | H | H |
| 206 | n-C₄H₉ | n-C₄H₉ | H | H |
| 207 | iso-C₄H₉ | iso-C₄H₉ | H | H |
| 208 | tert-C₄H₉ | tert-C₄H₉ | H | H |
| 209 | n-C₆H₁₃ | n-C₆H₁₃ | H | H |
| 210 | n-C₈H₁₇ | n-C₈H₁₇ | H | H |
| 211 | n-C₁₀H₂₁ | n-C₁₀H₂₁ | H | H |
| 212 | n-C₁₂H₂₅ | n-C₁₂H₂₅ | H | H |
| 213 | n-C₁₄H₂₉ | n-C₁₄H₂₉ | H | H |
| 214 | n-C₁₆H₃₃ | n-C₁₆H₃₃ | H | H |
| 215 | n-C₁₈H₃₇ | n-C₁₈H₃₇ | H | H |
| 216 | n-C₂₀H₄₁ | n-C₂₀H₄₁ | H | H |
| 217 | 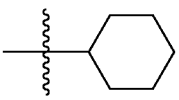 | 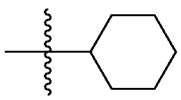 | H | H |
| 218 | 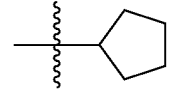 [SMILES: *C1CCCC1] | 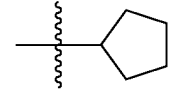 [SMILES: *C1CCCC1] | H | H |
| 219 | 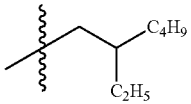 | 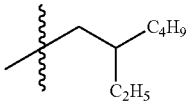 | H | H |
| 220 | 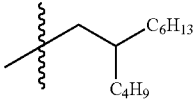 | 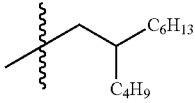 | H | H |
| 221 | 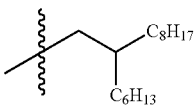 | 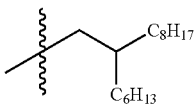 | H | H |
| 222 | 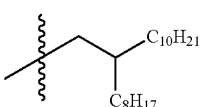 | 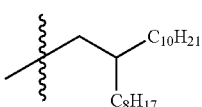 | H | H |
| 223 | 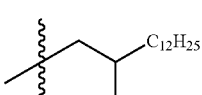 | 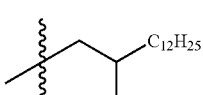 | H | H |
| 224 | 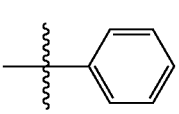 | 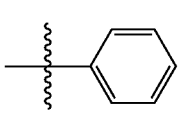 | H | H |
| 225 | 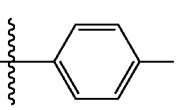 | 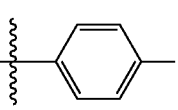 | H | H |
| 226 | 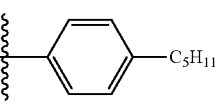 | 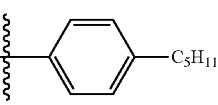 | H | H |

TABLE 2-continued

| | R₁ | R₂ | R₃ | R₄ |
|---|---|---|---|---|
| 227 | 4-C₈H₁₇-phenyl | 4-C₈H₁₇-phenyl | H | H |
| 228 | 2-thienyl | 2-thienyl | H | H |
| 229 | 5-C₈H₁₇-2-thienyl | 5-C₈H₁₇-2-thienyl | H | H |
| 230 | 5-C₁₂H₂₅-2-thienyl | 5-C₁₂H₂₅-2-thienyl | H | H |
| 231 | 2-pyridyl | 2-pyridyl | H | H |
| 232 | 2-naphthyl | 2-naphthyl | H | H |
| 233 | 1-naphthyl | 1-naphthyl | H | H |
| 234 | OCH₃ | OCH₃ | H | H |
| 235 | OC₈H₁₇ | OC₈H₁₇ | H | H |
| 236 | OC₁₂H₂₅ | OC₁₂H₂₅ | H | H |
| 237 | CO₂CH₃ | CO₂CH₃ | H | H |
| 238 | CO₂C₈H₁₇ | CO₂C₈H₁₇ | H | H |
| 239 | CO₂C₁₂H₂₅ | CO₂C₁₂H₂₅ | H | H |
| 240 | COCH₃ | COCH₃ | H | H |
| 241 | COC₈H₁₇ | COC₈H₁₇ | H | H |
| 242 | COC₁₂H₂₅ | COC₁₂H₂₅ | H | H |
| 243 | CN | CN | H | H |
| 244 | F | F | H | H |
| 245 | Cl | Cl | H | H |
| 246 | H | H | n-C₈H₁₇ | n-C₈H₁₇ |
| 247 | n-C₈H₁₇ | n-C₈H₁₇ | n-C₈H₁₇ | n-C₈H₁₇ |
| 248 | H | H | phenyl | phenyl |
| 249 | phenyl | phenyl | phenyl | phenyl |
| 250 | phenyl | n-C₈H₁₇ | H | H |

TABLE 2-continued

|  | R₁ | R₂ | R₃ | R₄ |
|---|---|---|---|---|
| 251 | (see structure) | n-C₈H₁₇ | H | H |

[Formula 12]

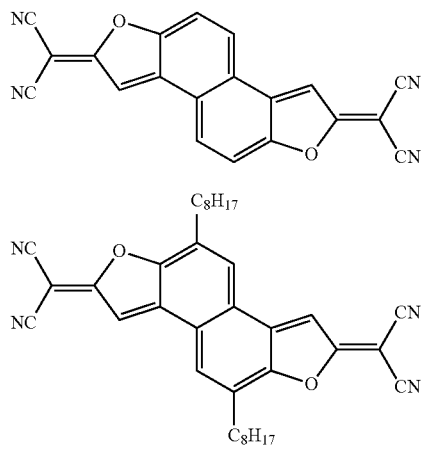

252

253

[Formula 13]

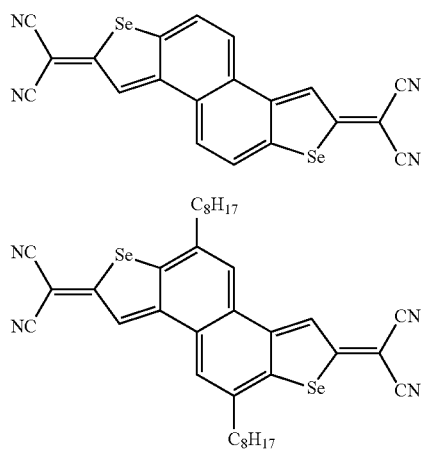

254

255

[Formula 14]

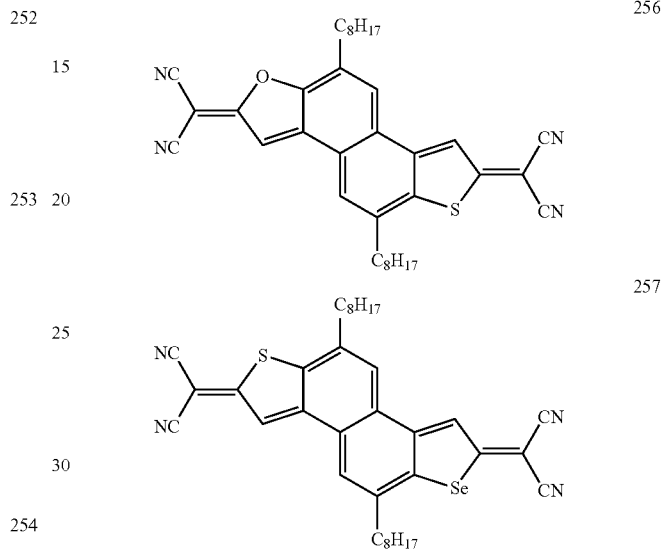

256

257

Table 3 shows compounds represented by general formula (7). The present invention is not to be limited thereto.

[Formula 15]

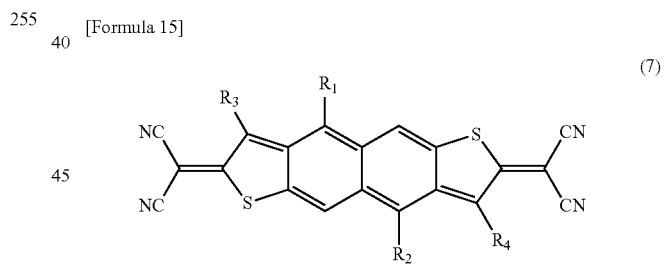

(7)

TABLE 3

|  | R₁ | R₂ | R₃ | R₄ |
|---|---|---|---|---|
| 301 | H | H | H | H |
| 302 | CH₃ | H | H | H |
| 303 | C₂H₅ | C₂H₅ | H | H |
| 304 | n-C₃H₇ | n-C₃H₇ | H | H |
| 305 | iso-C₃H₇ | iso-C₃H₇ | H | H |
| 306 | n-C₄H₉ | n-C₄H₉ | H | H |
| 307 | iso-C₄H₉ | iso-C₄H₉ | H | H |
| 308 | tert-C₄H₉ | tert-C₄H₉ | H | H |
| 309 | n-C₆H₁₃ | n-C₆H₁₃ | H | H |
| 310 | n-C₈H₁₇ | n-C₈H₁₇ | H | H |
| 311 | n-C₁₀H₂₁ | n-C₁₀H₂₁ | H | H |
| 312 | n-C₁₂H₂₅ | n-C₁₂H₂₅ | H | H |
| 313 | n-C₁₄H₂₉ | n-C₁₄H₂₉ | H | H |
| 314 | n-C₁₆H₃₃ | n-C₁₆H₃₃ | H | H |
| 315 | n-C₁₈H₃₇ | n-C₁₈H₃₇ | H | H |

TABLE 3-continued

| | $R_1$ | $R_2$ | $R_3$ | $R_4$ |
|---|---|---|---|---|
| 316 | n-$C_{20}H_{41}$ | n-$C_{20}H_{41}$ | H | H |
| 317 | cyclohexyl | cyclohexyl | H | H |
| 318 | cyclopentyl | cyclopentyl | H | H |
| 319 | –CH$_2$–CH($C_2H_5$)($C_4H_9$) | –CH$_2$–CH($C_2H_5$)($C_4H_9$) | H | H |
| 320 | –CH$_2$–CH($C_4H_9$)($C_6H_{13}$) | –CH$_2$–CH($C_4H_9$)($C_6H_{13}$) | H | H |
| 321 | –CH$_2$–CH($C_6H_{13}$)($C_8H_{17}$) | –CH$_2$–CH($C_6H_{13}$)($C_8H_{17}$) | H | H |
| 322 | –CH$_2$–CH($C_8H_{17}$)($C_{10}H_{21}$) | –CH$_2$–CH($C_8H_{17}$)($C_{10}H_{21}$) | H | H |
| 323 | –CH$_2$–CH($C_{10}H_{21}$)($C_{12}H_{25}$) | –CH$_2$–CH($C_{10}H_{21}$)($C_{12}H_{25}$) | H | H |
| 324 | phenyl | phenyl | H | H |
| 325 | 4-methylphenyl | 4-methylphenyl | H | H |
| 326 | 4-$C_5H_{11}$-phenyl | 4-$C_5H_{11}$-phenyl | H | H |
| 327 | 4-$C_8H_{17}$-phenyl | 4-$C_8H_{17}$-phenyl | H | H |
| 328 | thiophen-2-yl | thiophen-2-yl | H | H |
| 329 | 5-$C_8H_{17}$-thiophen-2-yl | 5-$C_8H_{17}$-thiophen-2-yl | H | H |

TABLE 3-continued

| | R₁ | R₂ | R₃ | R₄ |
|---|---|---|---|---|
| 330 | (5-dodecylthiophen-2-yl) | (5-dodecylthiophen-2-yl) | H | H |
| 331 | (pyridin-2-yl) | (pyridin-2-yl) | H | H |
| 332 | (naphthalen-2-yl) | (naphthalen-2-yl) | H | H |
| 333 | (naphthalen-1-yl) | (naphthalen-1-yl) | H | H |
| 334 | OCH₃ | OCH₃ | H | H |
| 335 | OC₈H₁₇ | OC₈H₁₇ | H | H |
| 336 | OC₁₂H₂₅ | OC₁₂H₂₅ | H | H |
| 337 | CO₂CH₃ | CO₂CH₃ | H | H |
| 338 | CO₂C₈H₁₇ | CO₂C₈H₁₇ | H | H |
| 339 | CO₂C₁₂H₂₅ | CO₂C₁₂H₂₅ | H | H |
| 340 | COCH₃ | COCH₃ | H | H |
| 341 | COC₈H₁₇ | COC₈H₁₇ | H | H |
| 342 | COC₁₂H₂₅ | COC₁₂H₂₅ | H | H |
| 343 | CN | CN | H | H |
| 344 | F | F | H | H |
| 345 | Cl | Cl | H | H |
| 346 | H | H | n-C₈H₁₇ | n-C₈H₁₇ |
| 347 | n-C₈H₁₇ | n-C₈H₁₇ | n-C₈H₁₇ | n-C₈H₁₇ |
| 348 | H | H | (phenyl) | (phenyl) |
| 349 | (phenyl) | (phenyl) | (phenyl) | (phenyl) |
| 350 | (phenyl) | n-C₈H₁₇ | H | H |
| 351 | (4-pentylphenyl) | n-C₈H₁₇ | H | H |

[Formula 16]

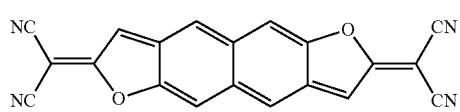

352

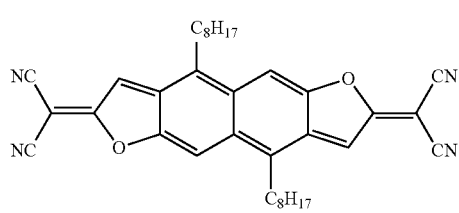

353

[Formula 17]

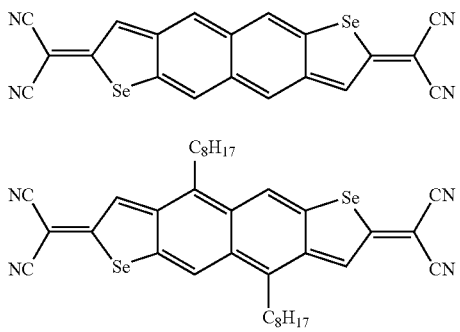

[Formula 18]

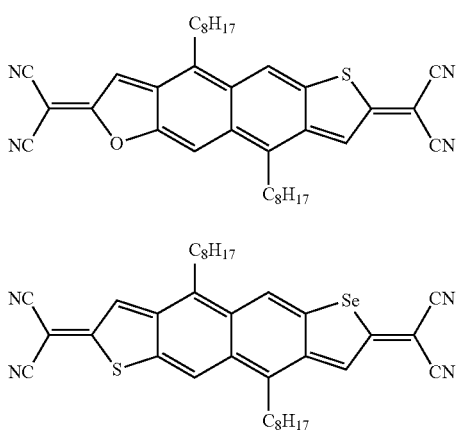

[Formula 19]

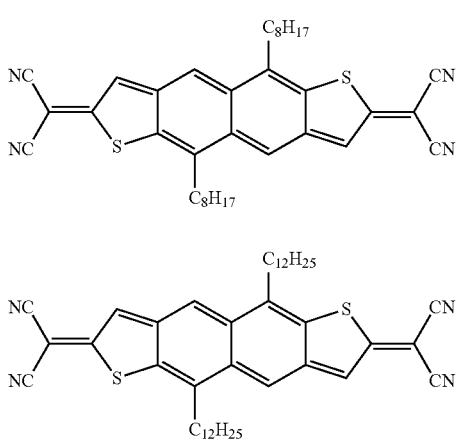

[Formula 20]

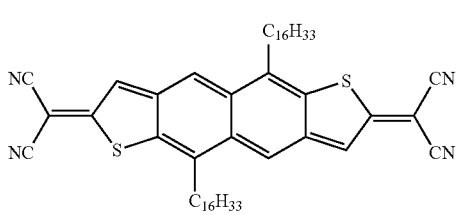

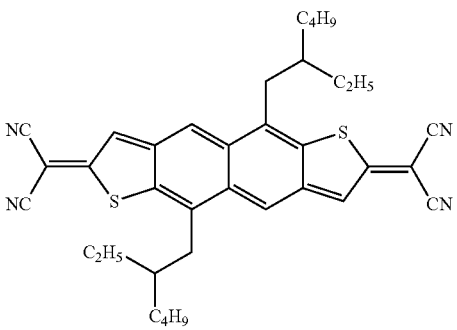

A composition for forming a thin film (hereinafter, often referred to as an organic semiconductor composition) according to the present description is a solution or dispersion containing a condensed polycyclic aromatic compound represented by general formula (1) in a solvent, and can contain other components unless the characteristics of the condensed polycyclic aromatic compound are impaired. The solvent is not especially limited as long as a composition containing the compound therein can form a film on a substrate, but is preferably an organic solvent, which may be a single kind of solvent or a mixture of two or more. The organic solvent includes halogenohydrocarbons such as dichloromethane, chloroform and dichloroethane; ethers such as diethyl ether, anisole and tetrahydrofuran; amides such as dimethylacetamide, dimethylformamide and N-methylpyrrolidone; nitriles such as acetonitrile, propionitrile and benzonitrile; alcohols such as methanol, ethanol, isopropanol and butanol; fluorinated alcohols such as octafluoropentanol and pentafluoropropanol; esters such as ethyl acetate, butyl acetate, ethyl benzoate and diethyl carbonate; aromatic hydrocarbons such as benzene, toluene, xylene, chlorobenzene, mesitylene, ethylbenzene, dichlorobenzene, chloronaphthalene and tetrahydronaphthalene; and hydrocarbons such as hexane, cyclohexane, octane, decane and tetralin.

The concentration of a condensed polycyclic aromatic compound represented by general formula (1) in an organic semiconductor composition may vary depending on the kind of a solvent and the thickness of a thin film formed, but may be preferably 0.001 part by weight to 20 parts by weight and more preferably 0.01 part by weight to 10 parts by weight, relative to 100 parts by weight of the solvent. If the compound is dissolved or dispersed in a solvent, it is sufficient for the organic semiconductor composition, but the compound may be preferably uniformly dissolved.

A thin film can be formed from an organic semiconductor composition containing a condensed polycyclic aromatic compound represented by general formula (1). The thickness of the thin film may vary depending on applications thereof, but may be usually 0.1 nm to 10 μm, preferably 0.5 nm to 3 μm, and more preferably 1 nm to 1 μm.

A method for forming a thin film may be generally conducted by a vacuum process such as a resistance heating deposition method, an electron beam deposition method, a sputtering method and a molecular lamination method; a solution process such as a spin coat method, a drop cast method, a dip coat method and a spray method; a letterpress printing method such as a flexographic printing method and a resin letterpress printing method; a planographic printing method such as an offset printing method, a dry offset printing method, a pad printing method; an intaglio printing method such as a gravure printing method; a stencil printing method such as a silk screen printing method, a mimeograph printing method and a lithographic printing method; a inkjet printing method; a micro contact printing method; and a combination thereof.

An organic electronic device can be fabricated by using a condensed polycyclic aromatic compound represented by general formula (1) as a material for electronics applications. Examples of the organic electronic devices include an organic transistor, a photoelectric conversion device, an organic solar cell device, an organic EL device, an organic light emitting transistor device and an organic semiconductor laser device. These will be described in detail.

First, an organic transistor will be described in detail.

An organic transistor has two electrodes (a source electrode and a drain electrode) in contact with an organic semiconductor, and controls the current flowing between the electrodes by a voltage applied to another electrode called a gate electrode.

Generally, organic transistor devices often have a structure in which a gate electrode is insulated with an insulating film (Metal-Insulator-Semiconductor, MIS structure). When a metal oxide film is used as the insulating film, the MIS structure is called a MOS structure. A different structure in which a gate electrode is formed via a Schottky barrier (MES structure) is available, but for organic transistors the MIS structure is often employed.

Hereinafter, organic transistors will be described in more detail with reference to drawings, but the present invention is not to be limited to these structures.

FIG. 1 illustrates some embodiments of organic transistor devices.

In each embodiment in FIG. 1, reference numeral 1 denotes a source electrode; 2 denotes a semiconductor layer; 3 denotes a drain electrode; 4 denotes an insulator layer; 5 denotes a gate electrode; and 6 denotes a substrate. It is to be noted that the arrangement of each layer and electrode can be suitably selected depending on applications of the device. A to D and F, in which current flows in the parallel direction to the substrate, are called a lateral transistor. A is called a bottom-contact bottom-gate structure; and B is called a top-contact bottom-gate structure. C has a source and a drain electrodes and an insulator layer on a semiconductor, and further a gate electrode on the insulator layer, and is called a top-contact top-gate structure. D is a structure called a top & bottom-contact bottom-gate type transistor. F is a bottom-contact top-gate structure. E is a schematic view of a transistor having a vertical structure, i.e. a static induction transistor (SIT). In this SIT, the flow of current spreads planarly, and a large amount of carriers can thus migrate at one time. Further, a source electrode and a drain electrode are vertically arranged, the distance between the electrodes can be thus shortened, so that the response speed is high. Therefore, the SIT can be preferably employed to allow a large current to flow or to enable a high-speed switching. It is to be noted that E of FIG. 1 depicts no substrate is depicted, but a substrate is usually provided outside the source or drain electrode represented by reference numerals 1 and 3 in FIG. 1E.

Each component in the each embodiment will be described.

A substrate 6 has to hold each layer formed thereon to prevent the each layer from coming off. For the substrate, the following materials can be used: an insulative material such as a resin plate or film, a paper, a glass, a quartz or a ceramic; a conductive substrate of a metal or an alloy on which an insulating layer is formed thereon by coating or the like; and a combination of resins, inorganic materials and others. A resin film can be, for example, of polyethylene terephthalate, polyethylene naphthalate, polyether sulfone, polyamide, polyimide, polycarbonate, cellulose triacetate or polyetherimide. A resin film or a paper can provide flexible and lightweight devices and improve their practicability. The thickness of a substrate is usually 1 µm to 10 mm, and preferably 5 µm to 5 mm.

For a source electrode 1, a drain electrode 3 and a gate electrode 5, conductive materials can be used. The material include, for example, metals such as platinum, gold, silver, aluminum, chromium, tungsten, tantalum, nickel, cobalt, copper, iron, lead, tin, titanium, indium, palladium, molybdenum, magnesium, calcium, barium, lithium, potassium and sodium, and alloys containing these; conductive oxides such as $InO_2$, $ZnO_2$, $SnO_2$ and ITO; conductive polymer compounds such as polyaniline, polypyrrole, polythiophene, polyacethylene, polyparaphenylenevinylene and polydiacetylene; inorganic semiconductors such as silicon, germanium and gallium arsenide; and carbon materials such as carbon black, fullerene, carbon nanotubes, graphite and graphene. The conductive polymer compounds and the semiconductors may be doped. Examples of the dopant include inorganic acids such as hydrochloric acid and sulfuric acid; organic acids having an acidic functional group, such as sulfonic acid; Lewis acids such as $PF_5$, $AsF_5$ and $FeCl_3$; halogen atoms such as iodine; and metal atoms such as lithium, sodium and potassium. Boron, phosphorus, arsenic and the like can be used as a dopant for inorganic semiconductors such as silicon.

Used also are conductive composite materials in which carbon black, metal particles or the like are dispersed in the above-mentioned dopant. In order to reduce the contact resistance of a source electrode 1 and a drain electrode 3, which are in direct contact with a semiconductor, it is important to select an appropriate work function or to treat the surfaces.

The distance (channel length) between a source electrode and a drain electrode is an important factor to determine the characteristics of a device. The channel length is usually 0.01 to 300 µm and preferably 0.1 to 100 µm. The shorter the channel length, the larger the amount of current extracted. However, it causes the short channel effect such as the influence of the contact resistance, which makes it difficult to control the device. An appropriate channel length is thus needed. The width (channel width) between a source and drain electrodes is usually 10 to 10,000 µm and preferably 100 to 5,000 µm. However, it is possible to further widen the channel width, for instance, by an electrode having a comb-like structure. After all, it is preferable to select an appropriate width depending on the amount of current required, the structure of a device or others.

The respective structures (shapes) of a source electrode and a drain electrode will be described. The structures of a source electrode and a drain electrode may be identical or different.

In the case of a bottom-contact structure, each electrode is generally fabricated by lithography, and the each electrode is preferably formed in a rectangular parallelepiped. Various types of printing methods has recently improved in terms of printing precision, and electrodes have been able to be fabricated well precisely by inkjet printing, gravure printing, screen printing or the like. In the case of a top-contact structure in which electrodes are on a semiconductor, the electrodes can be vapor-deposited using a shadow mask or the like. Electrode patterns have been able to be directly printed and formed by inkjet, or the like. The length of the electrodes is the same as the channel width mentioned above. The width of the electrodes is not particularly specified, but preferably smaller to make the area of a device smaller, provided that the electric properties are stable. The width of the electrodes is usually 0.1 to 1,000 μm and preferably 0.5 to 100 μm. The thickness of the electrodes is usually 0.1 to 1,000 nm, preferably 1 to 500 nm, and more preferably 5 to 200 nm. The electrode 1, 3 and 5 are each connected to a wire, which is fabricated of nearly the same material as those of the electrodes.

For an insulator layer 4, an insulating material can be used. The material includes, for example, polymers such as polyparaxylylene, polyacrylate, polymethyl methacrylate, polystyrene, polyvinylphenol, polyamide, polyimide, polycarbonate, polyester, polyvinyl alcohol, polyvinyl acetate, polyurethane, polysulfone, fluororesins, epoxy resins and phenol resins, and copolymers in combinations thereof; metal oxides such as silicon oxide, aluminum oxide, titanium oxide and tantalum oxide; ferroelectric metal oxides such as $SrTiO_3$ and $BaTiO_3$; dielectrics such as nitrides, e.g. silicon nitride and aluminum nitride, sulfides and fluorides; and polymers in which particles of these dielectrics are dispersed. For the insulator layer, a material having a high electric insulation property can be preferably used in order to make leak current small. Such a material allows the film thickness to be small and the insulation capacity to be large, whereby the amount of extractable current can increase. Further, to improve the mobility of the semiconductor, it is preferable that the surface energy of the insulator layer is reduced and the layer has a smooth surface with no unevenness. For this purpose, a self-organized unimolecular film or a two-layered insulator layer may be formed. The film thickness (in the case of two or more layers, meaning the entire film thickness) of an insulator layer 4 may vary depending on the material, but be usually 0.1 nm to 100 μm, preferably 0.5 nm to 50 μm, and more preferably 1 nm to 10 μm.

As a material of a semiconductor layer 2, a condensed polycyclic aromatic compound represented by general formula (1) according to the present invention can be used. A semiconductor layer 2 is formed as a thin film by the method described before. For the purpose of improving the properties of an organic transistor, or imparting other properties thereto, other organic semiconductor materials or various types of additives may be mixed as appropriate.

For an organic transistor, at least one of condensed polycyclic aromatic compounds represented by general formula (1) can be used as an organic semiconductor material. In the case where a thin film of a compound represented by the general formula (1) is formed by a solution process, that is, in the case of using a solvent, it is preferable that the thin film is used after the solvent is substantially evaporated. For the purpose of improving the properties of a transistor, or the like, additives such as a dopant may be contained.

The additives may be usually contained in the range of 0.01 to 10 parts by weight, preferably 0.05 to 5 parts by weight, and more preferably 0.1 to 3 parts by weight, relative to 100 parts by weight of the solvent.

Further, the semiconductor layer may be composed of a multi-layer structure, but more preferably of a single layer structure. The film thickness of a semiconductor layer 2 is preferably as thin as possible unless the necessary functions are lost. This is because in the lateral organic transistors shown in A, B and D, where the layer has a predetermined thickness or more thickness, the properties of the devices do not depend on the film thickness, whereas the greater the film thickness, the more the leak current in many cases. To exhibit necessary functions, the film thickness of a semiconductor layer is usually 1 nm to 1 μm, preferably 5 nm to 500 nm, and more preferably 10 nm to 300 nm.

For organic transistors, as required, other layers can be provided, for example, between a substrate layer and an insulating film layer, between an insulating film layer and a semiconductor layer, or on the outer surfaces of a device. For example, a protection layer which is formed directly or through another layer on an organic semiconductor layer, allows the influence of the air outside such as humidity to be reduced. The layer also provide an advantage of stabilizing the electric properties of an organic transistor device, including an increased on/off ratio thereof.

The material of a protection layer is not especially limited, but preferably includes various types of resins such as epoxy resins, acryl resins, e.g. polymethyl methacrylate or the like, polyurethane, polyimide, polyvinyl alcohol, fluororesins and polyolefin; inorganic oxides such as silicon oxide, aluminum oxide, silicon nitride or the like; and dielectrics such as nitrides; and particularly resins (polymers) having a low permeability of oxygen and moisture and a low water absorption. Gas-barrier protection materials developed for organic EL displays can also be used. The film thickness of a protection layer can be selected according to its purpose, but be usually 100 nm to 1 mm.

Further, a substrate or an insulator layer on which an organic semiconductor layer is to be stacked may be subjected to a surface modification or a surface treatment in advance, which can improve transistor properties of the organic transistor device. For instance, the degree of hydrophilicity/hydrophobicity of the substrate surface can be controlled, which may improve the film quality and the film formability of a film to be formed on the substrate. The properties of an organic semiconductor material may largely vary particularly depending on the film conditions such as molecular orientation. In this regard, the surface treatment to a substrate, an insulator layer or the like could control the molecular orientation of the interfacial portion with an organic semiconductor layer to be subsequently formed, or reduce trap sites on a substrate or an insulator layer, thereby improving the properties such as carrier mobility.

The trap site refers to a functional group such as a hydroxyl group which is present on an untreated substrate. If such a functional group is present, electrons are attracted to the functional group, and the carrier mobility consequently decreases. Therefore, decrease in trap sites would be effective for the improvement of the properties including carrier mobility in many cases.

Examples of the surface treatment to improve the properties as described above include a self-organized unimolecular film treatment with hexamethyldisilazane, octyltrichlorosilane, octadecyltrichlorosilane or the like; a surface treatment with a polymer or the like; an acid treatment with hydrochloric acid, sulfuric acid, acetic acid or the like; an alkali treatment with sodium hydroxide, potassium hydroxide, calcium hydroxide, ammonia or the like; an ozone treatment; a fluorination treatment; a plasma treatment with oxygen, argon or the like; a treatment of forming a Langmuir-Blodgett film; a treatment of forming a thin film of another insulator or a semiconductor; a mechanical treatment; an electric treatment with corona discharge or the like; a rubbing treatment with fibers or the like; and combinations thereof.

In these embodiments, methods for providing, for example, each of a substrate layer and a insulating film layer, or each of an insulating film layer and an organic semiconductor layer can suitably be selected from the above-mentioned vacuum processes and solution processes.

Then, a method for producing an organic transistor device according to the present invention will be described taking as an example the top-contact bottom-gate type organic transistor in the embodiment B of FIG. 1 and making reference to FIG. 2. This method can be similarly applied to organic transistors of the other embodiments described before, and the like.

(Substrate of an Organic Transistor, and Substrate Treatment)

Figure 2:
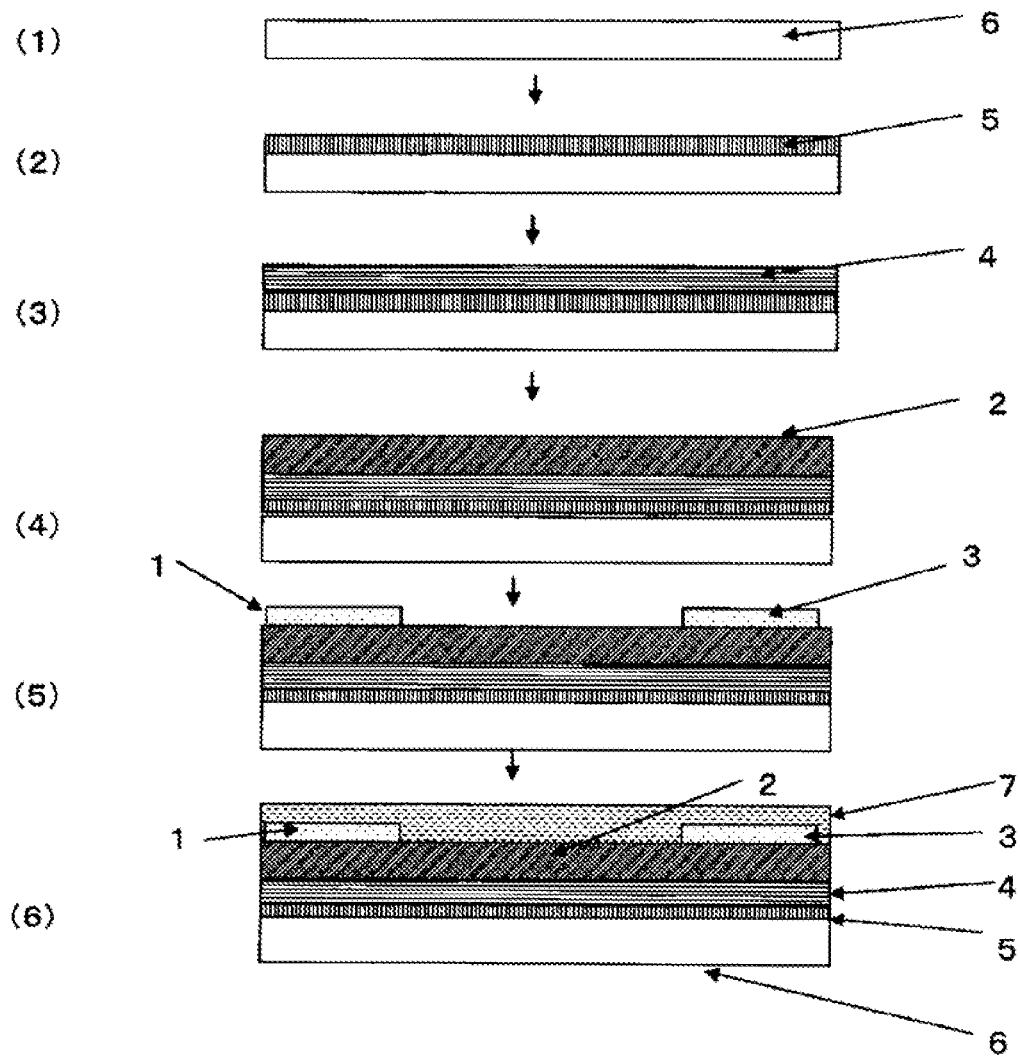
FIG. 2 is a schematic view illustrating a process of producing an organic transistor according to an embodiment of the present invention.

An organic transistor according to the present invention is fabricated by providing various types of necessary layers and electrodes on a substrate 6 (see FIG. 2(1)). A substrate as described above can be used. The above-mentioned surface treatment may be carried out on the substrate. The thickness of a substrate 6 is preferably as small as possible unless the necessary characteristics are impaired. The thickness may vary depending on the material, but be usually 1 µm to 10 mm, and preferably 5 µm to 5 mm. As required, the substrate may be allowed to have the function of an electrode.

(Gate Electrode Formation)

A gate electrode 5 is formed on the substrate 6 (see FIG. 2(2)). An electrode material as described above may be used. To form an electrode film, various types of methods can be used, and there are employed, for example, a vacuum deposition method, a sputtering method, a coating method, a thermal transfer method, a printing method, and a sol-gel method. During or after film formation, preferably, patterning is carried out, as required, so as to allow the electrode to be in a desired shape. Various types of patterning methods can be used. Examples thereof include photolithography in which patterning with a photo resist and etching are combined. Patterning may be also carried out by a vapor deposition process with a shadow mask, a sputtering process, a printing methods such as an inkjet printing method, a screen printing method, an offset printing method and a letterpress printing process, a soft lithography method such as a micro contact printing method, and a combinations thereof. The film thickness of a gate electrode 5 may vary depending on the material, but be usually 0.1 nm to 10 µm, preferably 0.5 nm to 5 µm, and more preferably 1 nm to 3 µm. In the case that a gate electrode also serves as a substrate, the thickness may be larger than the above-mentioned film thickness.

(Insulator Layer Formation)

An insulator layer 4 is formed on the gate electrode 5 (see FIG. 2(3)). An insulator material as described above can be used. To form an insulator layer 4, various types of methods can be used. Examples thereof include coating methods such as a spin coating method, a spray coating method, a dip coating method, a casting method, a bar coating method and a blade coating method; printing methods such as a screen printing method, an offset printing method and an inkjet method; and dry processes such as a vacuum deposition method, a molecular beam epitaxial growth method, an ion cluster beam method, an ion plating method, a sputtering method, an atmospheric plasma method and a CVD method. There are additionally employed a sol-gel method, a method in which an oxide film is formed on a metal, like alumite on aluminum and silicon oxide on silicon, by a thermal oxidation method or the like, and other methods. Here, at the portion where an insulator layer comes in contact with a semiconductor layer, the insulator layer may be subjected to a surface treatment in order to allow molecules constituting the semiconductor, for example, molecules of a condensed polycyclic aromatic compound represented by formula (1) to be well oriented at the interface between the layers. The same surface treatments as those for the substrate can be applied. The thickness of an insulator layer 4 is preferably as small as possible because such a thin layer increases the electric capacity and allows the electric amount to be extracted to be increased. In this regard, a thinner film tends to cause leak current to be increased, and the thickness may be preferably smaller in the range of not impairing its function. The thickness is usually 0.1 nm to 100 µm, preferably 0.5 nm to 50 µm, and more preferably 5 nm to 10 µm.

(Organic Semiconductor Layer Formation)

The organic semiconductor material containing the condensed polycyclic aromatic compound represented by the general formula (1) according to the present invention is used for the formation of the organic semiconductor layer (see FIG. 2(4)). For the film formation of the organic semiconductor layer, various types of methods can be used. The formation methods specifically include vacuum processes such as a sputtering method, a CVD method, a molecular beam epitaxial growth method and a vacuum deposition method; coating methods such as a dip coat method, a die coater method, a roll coater method, a bar coater method and a spin coat method; and solution processes such as an inkjet method, a screen printing method, an offset printing method and a micro contact printing method.

First, a method for forming as a film the organic semiconductor material by a vacuum process to thereby obtain the organic semiconductor layer will be described. As the film formation method by a vacuum process, there is preferably employed a method in which the organic semiconductor material is heated in a crucible or a metal boat under vacuum, and the evaporated organic semiconductor material is deposited (vapor deposited) on the substrate (the substrate, the insulator layer, the source electrode, the drain electrode or the like), that is, a vacuum deposition method. At this time, the degree of vacuum is usually $1.0 \times 10^{-1}$ Pa or lower, and preferably $1.0 \times 10^{-3}$ Pa or lower. Further since the properties of the organic semiconductor film, in its turn, of the organic transistor varies in some cases depending on the substrate temperature in the vapor deposition time, it is preferable that the substrate temperature is cautiously selected. The substrate temperature in the vapor deposition time is usually 0 to 200° C., preferably 5 to 180° C., more preferably 10 to 150° C., still more preferably 15 to 120° C., and especially preferably 20 to 100° C.

Further the deposition rate is usually 0.001 nm/sec to 10 nm/sec, and preferably 0.01 nm/sec to 1 nm/sec. The film thickness of the organic semiconductor layer formed of the organic semiconductor material is usually 1 nm to 1 µm, preferably 5 nm to 500 nm, and more preferably 10 nm to 300 nm.

Here, in place of the deposition method in which the organic semiconductor material to form the organic semiconductor layer is heated, evaporated and deposited on the substrate, other means may be used.

Then, a method for forming a film by a solution process to thereby obtain the organic semiconductor layer will be described. A composition prepared by dissolving the condensed polycyclic aromatic compound represented by the general formula (1) according to the present invention in a solvent or the like, and as required, adding additives and the like is applied on the substrate (exposed portions of the insulator layer, the source electrode and the drain electrode). The application method includes spin coat methods, drop cast methods, dip coat methods and spray methods, letterpress printing methods such as flexographic printing and resin letterpress printing, planographic printing methods such as an offset printing method, a dry offset printing method and a pad printing method, intaglio printing methods such as a gravure printing method, stencil printing methods such as a silk screen printing method and a mimeograph printing method and a lithographic printing method, inkjet printing methods, micro contact printing methods, and methods in combinations of these means.

As methods similar to the applying method, there can also be employed a Langmuir-Blodgett method in which a unimolecular film of the organic semiconductor layer fabricated by dropping the above composition on a water surface is transferred and laminated on a substrate, a method in which a liquid crystal or a material in a melt state is interposed between two substrates and introduced therebetween by the capillary phenomenon, or the like.

The environment including the temperature of the substrate and the composition in the film forming time is also important; since the properties of the transistor vary by the temperature of the substrate and the composition in some cases, it is preferable that the temperature of the substrate and the composition needs to be cautiously selected. The substrate temperature is usually 0 to 200° C., preferably 10 to 120° C., and more preferably 15 to 100° C. The caution is needed because the temperature to be selected depends largely on a solvent in a composition to be used and the like.

It is better that the film thickness of the organic semiconductor layer fabricated by this method is thinner in the range of not impairing the functions. When the film thickness is large, there arises a risk of the leak current becoming large. The film thickness of the organic semiconductor layer is usually 1 nm to 1 µm, preferably 5 nm to 500 nm, and more preferably 10 nm to 300 nm.

The organic semiconductor layer (see FIG. 2(4)) thus formed is allowed to be further improved in the properties by a post-treatment. The improvement and the stabilization of the organic semiconductor properties can be achieved, for example, by a heat treatment, for reasons that the heat treatment relaxes strains in the film generated during the film formation, reduces pinholes and the like, can control the arrangement and orientation in the film, and otherwise. Carrying out the heat treatment in fabrication of the organic transistor according to the present invention is effective for the improvement of the properties. The heat treatment is carried out by heating the substrate after the organic semiconductor layer is formed. The temperature of the heat treatment is not especially limited, but usually from room temperature to about 150° C., preferably 40 to 120° C., and more preferably 45 to 100° C. The heat treatment time at this time is not especially limited, but usually 10 sec to 24 hours, and preferably about 30 sec to 3 hours. The atmosphere at this time may be the air, but may be an inert atmosphere such as nitrogen or argon. Additionally, the control and the like of the film shape by a solvent vapor are allowed.

By a treatment, as another post-treatment of the organic semiconductor layer, of using an oxidative or reductive gas such as oxygen or hydrogen, an oxidative or reductive liquid, or the like, the variation in the properties due to oxidation or reduction can also be induced. This can be utilized, for example, for the purpose of an increase or decrease in the carrier density in the film.

Further in the means called doping, by adding elements, atomic groups, molecules and polymers in minute amounts to the organic semiconductor layer, the properties of the organic semiconductor layer can be varied. There can be doped, for example, oxygen, hydrogen, acids such as hydrochloric acid, sulfuric acid and sulfonic acid; Lewis acids such as $PF_5$, $AsF_5$ and $FeCl_3$; halogen atoms such as iodine; metal atoms such as sodium and potassium; and donor compounds such as tetrathiafulvalene (TTF) and phthalocyanine This can be achieved by bringing these gases into contact with the organic semiconductor layer, immersing it in a solution, or subjecting it to an electrochemical doping treatment. These doping treatments may not be after the fabrication of the organic semiconductor layer, but the doping materials may be added in the synthesis time of the organic semiconductor compound, or in the process of fabricating the organic semiconductor layer by using a composition for fabrication of an organic semiconductor device, may be added to the composition or to a thin film in the step of forming the thin film. Doping materials may be added to a material to form the organic semiconductor layer and co-deposited in the vapor deposition time; doping materials are mixed in the surrounding atmosphere in the fabrication time of the organic semiconductor layer (the organic semiconductor layer is fabricated under the environment in which doping materials are present); or further ions may be accelerated in a vacuum and made to collide with and doped in a film.

The effects of these doping treatments include a variation in the electroconductivity due to an increase or decrease in the carrier density, a change (p-type, n-type) of the polarity of the carriers, and a shift in the Fermi level.

(The Formation of the Source Electrode and the Drain Electrode)

The formation method and the like of the source electrode 1 and the drain electrode 3 are according to the case of the gate electrode 5 (see FIG. 2(5)). Further in order to reduce the contact resistance with the organic semiconductor layer, various types of additives are allowed to be used.

(Protection Layer)

When the protection layer 7 is formed on the organic semiconductor layer, the influence of the air atmosphere can be minimized, and there is also brought about an advantage of being capable of stabilizing the electric properties of the organic transistor (see FIG. 2(6)). As the material for the protection layer, the above material is used. An optional film thickness can be employed according to the purpose, but the thickness of the protection layer 7 is usually 100 nm to 1 mm.

For formation of the film of the protection layer, various types of methods can be employed, but in the case where the protection layer is composed of a resin, examples of the methods include a method in which a resin solution is applied, and thereafter dried to thereby make a resin film; and a method in which a resin monomer is applied or vapor deposited, and thereafter polymerized. After the film forming, a crosslinking treatment may be carried out.

In the case where the protection layer is composed of an inorganic substance, there can be used, for example, formation methods in vacuum processes such as a sputtering method and a vapor deposition method, and formation methods in solution processes such as a sol-gel method.

In the organic transistor, in addition to on the organic semiconductor layer, as required, a protection layer may be provided further between each layer. These layers are helpful in stabilizing the electric properties of the organic transistor in some cases.

Since the condensed polycyclic aromatic compound represented by the general formula (1) is used as the organic semiconductor material, the organic transistor can be produced in a comparatively low-temperature process. Therefore, flexible materials such as plastic plates and plastic films, which cannot be used under the condition of being exposed to high temperatures, can be used as the substrate. As a result, devices which are lightweight and excellent in flexibility are enabled to be produced, and can be utilized as switching devices of active matrices of displays, and the like.

The organic transistor can be utilized also as digital devices and analog devices such as memory circuit devices, signal driver circuit devices and signal processing circuit devices. By further combining these, fabrication of displays, IC cards, IC tags and the like is enabled. Further the organic transistor, since being able to causing variations in its properties due to external stimuli such as chemical substances, can be utilized as sensors.

Then, the organic EL device will be described.

Organic EL devices are paid attention to in being able to be utilized in applications such as solid, self-luminescent large-area color displays and lightings, and have been developed much. As their constitutions, there are known a device having a structure having two layers of a luminescent layer and a charge transport layer provided between opposing electrodes composed of an anode and a cathode; a device having a structure having three layers of an electron transport layer, a luminescent layer and a hole transport layer stacked between the opposing electrodes; and a device having a structure having three or more layers, and there are further known a device having a structure having a single layer of a luminescent layer, and the like.

The condensed polycyclic aromatic compound represented by the general formula (1) can be utilized as an electron transport layer.

(Photoelectric Conversion Device)

By utilizing the semiconductor properties of the condensed polycyclic aromatic compound represented by the general formula (1) according to the present invention, the utilization thereof as an organic photoelectric conversion device is enabled. The photoelectric conversion device includes charge coupled devices (CCD) having a function of converting picture signals of motion pictures, still pictures and the like to digital signals, as image sensors being solid-state image pick-up devices; and the development of organic photoelectric conversion devices is also anticipated which are more inexpensive and make the best use of the large area-making processability, the flexible function intrinsic to organic substances, and the like.

(Organic Solar Cell Device)

By using the condensed polycyclic aromatic compound represented by the general formula (1) according to the present invention, a flexible, low-cost organic solar cell device can be fabricated simply. The organic solar cell device is a solid device, and excellent in the flexibility and the point of the improved service life. Although the development of solar cells using organic thin film semiconductors in combinations of electroconductive polymers, fullerene and the like is conventionally in the mainstream, there arises a problem with the power generation conversion efficiency.

Generally, the constitution of organic solar cell devices is, similar to silicon-based solar cells, such that a layer (power generation layer) to generate a power is interposed between a anode and a cathode, and positive holes and electrons generated due to light absorption are received by corresponding electrodes to thereby function as solar cells. The power generation layer is constituted of a p-type donor material and an n-type acceptor material, and other materials for a buffer layer and the like. Here, solar cells in which as the materials therefor, organic materials are used are called organic solar cells.

Figure 3:
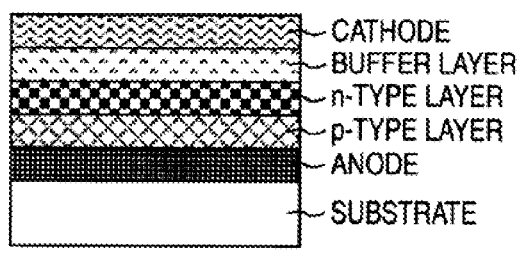
FIG. 3 is a schematic view illustrating a structure applied to a photoelectric conversion device and a solar cell.

Junction structures include Schottky junctions, heterojunctions, bulk heterojunctions, nano-structure junctions and hybrids; each material efficiently absorbs incident light and generates charges, and the generated charges (positive holes and electrons) are separated, transported and collected to thereby function as solar cells. Here, the structure of one example of a heterojunction device, which is a structure of usual solar cells, is illustrated in FIG. 3.

Then, the constituting elements in the organic solar cell device will be described.

A anode and a cathode in the organic solar cell device are the same as the electrode materials of the organic transistor as described before. In order to efficiently take in light, it is desirable that the electrodes are made to be ones having transparency in the absorption wavelength region of the power generation layer. Further in order for the organic solar cell device to have good solar cell properties, it is preferable that the electrodes have a sheet resistance of 20 Ω/square or lower, and a light transmittance of 85% or higher.

The power generation layer is formed at least of one layer of or a plurality of layers of an organic thin film containing a compound represented by the general formula (1) according to the present invention. Although the organic solar cell device is allowed to assume the structure described before, the device is fundamentally constituted of a p-type donor material, an n-type acceptor material and a buffer layer.

The p-type donor material is fundamentally a compound capable of transporting positive holes, and includes π-conjugated polymers such as polyparaphenylene vinylene derivatives, polythiophene derivatives, polyfluorene derivatives and polyaniline derivatives, carbazole, and other polymers having heterocyclic side chains. The compound further includes low-molecular compounds such as pentacene derivatives, rubrene derivatives, porphyrin derivatives, phthalocyanine derivatives, indigo derivatives, quinacridone derivatives, merocyanine derivatives, cyanine derivatives, squarylium derivatives and benzoquinone derivatives.

Condensed polycyclic aromatic compounds of the general formula (1) can suitably be used as an n-type acceptor material. This acceptor material can be used singly, but may be used as a mixture thereof with other acceptor materials. The acceptor material to be mixed is fundamentally a compound capable of transporting electrons, and includes electroconductive high-molecular materials such as oligomers or polymers having pyridine and its derivatives in their skeletons, oligomers or polymers having quinoline and its derivatives in their skeletons, polymers having benzophenanthrolines and their derivatives, and cyano-polyphenylene vinylene derivatives (CN-PPV and the like), and electroconductive low-molecular materials such as fluorinated phthalocyanine derivatives, perylene derivatives, naphthalene derivatives, bathocuproine derivatives, and fullerene derivatives such as C60, C70 and PCBM.

It is preferable that the material efficiently absorbs light and generates charges, and it is preferable that the material to be used has a high light absorptivity.

A method for forming a thin film for the power generation layer of the organic solar cell is similar to the method described in the paragraph of the organic transistor device described before. Although it is better that the thickness of the thin film, though depending on the constitution of the solar cell, is thicker in order to sufficiently absorb light and prevent short-circuit, since it is better that the distance for transporting charges generated is shorter, a thinner thickness thereof is more suitable. Generally, the thickness as the power generation layer is preferably about 10 to 500 nm.

(Organic Semiconductor Laser Device)

Since the condensed polycyclic aromatic compound represented by the general formula (1) is a compound having organic semiconductor properties, the compound is anticipated to be utilized as an organic semiconductor laser device.

That is, when a resonator is incorporated to the organic semiconductor device containing the condensed polycyclic aromatic compound represented by the general formula (1), and the density of the excitation state can be sufficiently raised by efficiently injecting carriers, it is anticipated that light is amplified and the organic semiconductor device brings about the laser oscillation. Although, conventionally, only the laser oscillation by the light excitation is observed, and it is considered that high-density carriers are injected to an organic semiconductor device and a high-density excitation state is generated, which is considered to be necessary for the laser oscillation by the electric excitation, by using the organic semiconductor device containing the condensed polycyclic aromatic compound represented by the general formula (1) according to the present invention, the possibility of causing a high-efficiency luminescence (electroluminescence) is anticipated.

EXAMPLES

Synthesis of condensed polycyclic aromatic compounds represented by general formulae (8) and (9)

[Formula 21]

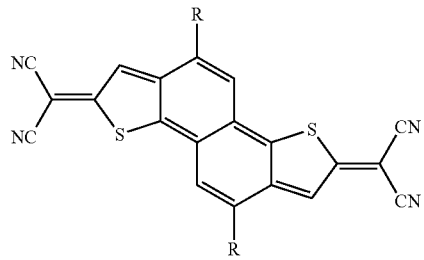

(8)

[Formula 22]

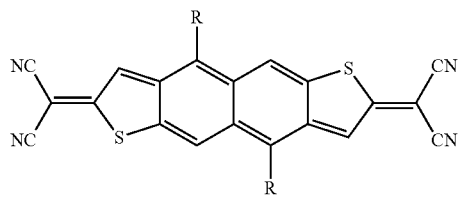

(9)

Specific examples of the synthesis of condensed polycyclic aromatic compounds represented by general formulae (8) and (9) will be described below. Here, in the following process, dry distilled solvents were used for reactions and measurements in inert gases; and commercially available first-grade or special-grade solvents were used for other reactions and operations. Reagents, as required, were refined with dry distillation or the like; and otherwise, commercially available first-grade or special-grade reagents were used. Disogel IR-60 (silica gel, active) and MERCK Art 1097 Aluminiumoxide 90 (alumina, active) were used for column chromatography purification; and Silicagel 60F254 (MERCK) was used for TLC. Solvents were distilled off by a rotary evaporator. Analysis instruments and measurement instruments are shown below.

Nuclear magnetic resonance spectrometry (hereinafter, referred to as "1H-NMR") was conducted by LAMBDA-NMR (395.75 MHz, å value, ppm, internal standard: TMS). Mass spectrometry (hereinafter, referred to as "MS") was conducted by MALDI-MS KRATOS ANALYTICAL KOMPACT MALDI, Shimadzu GCMS-QP5050 mass spectrometer.

Example 1

Malononitrile (1.7 mmol), THF (5 mL) and sodium hydride (2 2 mmol) were added to a 20-mL two-necked flask and stirred for 30 min under a nitrogen atmosphere. Then, 2,7-dibromo-5,10-dioctylnaphtho[1,2-b:5,6-b']dithiophene (0.3 mmol) and Pd(PPh$_3$)$_4$ (0.07 mmol) were added and refluxed for 15 hours. After the reaction was completed, the resultant was allowed to cool to room temperature; a small amount of 1N hydrochloric acid was added; and the precipitated solid was filtered off. Then, the obtained solid was dissolved in dichloromethane (10 mL); 2,3-dichloro-5,6-dicyano-p-benzoquinone was added, and thereafter heated to 80° C. The resultant was allowed to cool to room temperature; and the precipitated solid was filtered off to thereby obtain Compound 110 as a deep green solid.

[Formula 23]

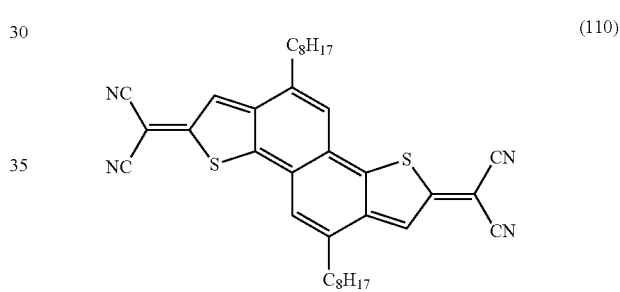

(110)

Compound 110 was obtained in a yield of 47%.

Measurement Result:

1H-NMR (400 MHz, CDCl$_3$) δ 0.97 (t, 6H), 1.24-1.42 (m, 20H), 1.71 (Quin, 4H), 2.78 (t, 4H) 7.05 (s, 2H), 7.57 (s, 2H)

Example 2

Compound 112 was obtained by the same process as in Example 1, except for using 2,7-dibromo-5,10-didodecyl-naphtho[1,2-b:5,6-b']dithiophene in place of 2,7-dibromo-5,10-dioctylnaphtho[1,2-b:5,6-b']dithiophene in Example 1.

[Formula 24]

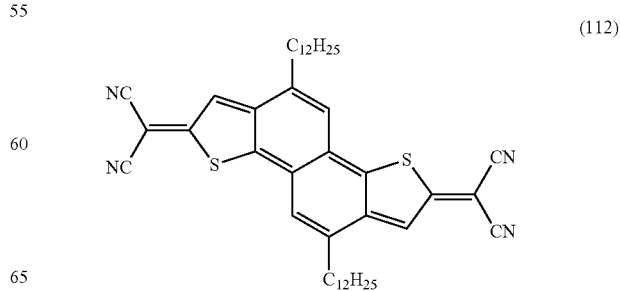

(112)

The compound 112 was obtained in a yield of 40%.
Measurement Result:
1H-NMR (400 MHz, CDCl$_3$) δ 0.97 (t, 6H), 1.24-1.42 (m, 36H), 1.71 (Quin, 4H), 2.78 (t, 4H) 7.05 (s, 2H), 7.57 (s, 2H)

Example 3

Compound 114 was obtained by the same process as in Example 1, except for using 2,7-dibromo-5,10-dihexadecyl-naphtho[1,2-b:5,6-b']dithiophene in place of 2,7-dibromo-5,10-dioctylnaphtho[1,2-b:5,6-b']dithiophene in Example 1.

[Formula 25]

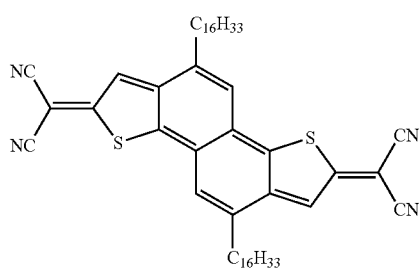

(114)

Compound 114 was obtained in a yield of 48%.
Measurement Result:
1H-NMR (400 MHz, CDCl$_3$) δ 0.97 (t, 6H), 1.24-1.42 (m, 52H), 1.71 (Quin, 4H), 2.78 (t, 4H) 7.05 (s, 2H), 7.57 (s, 2H)

Example 4

Compound 119 was obtained by the same process as in Example 1, except for using 2,7-dibromo-5,10-bis(2-ethylhexyl)naphtho[1,2-b:5,6-b']dithiophene in place of 2,7-dibromo-5,10-dioctylnaphtho[1,2-b:5,6-b']dithiophene in Example 1

[Formula 26]

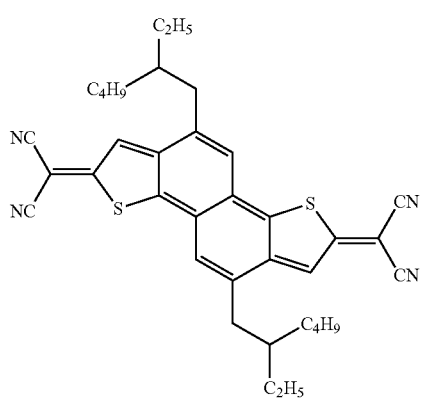

(119)

Compound 119 was obtained in a yield of 46%.
Measurement Result:
1H-NMR (400 MHz, CDCl$_3$) δ 0.91 (t, 6H), 0.95 (t, 6H), 1.24-1.42 (m, 16H), 1.71 (m, 2H), 2.71 (d, 4H) 7.05 (s, 2H), 7.57 (s, 2H)

Example 5

Compound 123 was obtained by the same process as in Example 1, except for using 2,7-dibromo-5,10-bis(4-ethyloctyl)naphtho[1,2-b:5,6-b']dithiophene in place of 2,7-dibromo-5,10-dioctylnaphtho[1,2-b:5,6-b']dithiophene in Example 1.

[Formula 27]

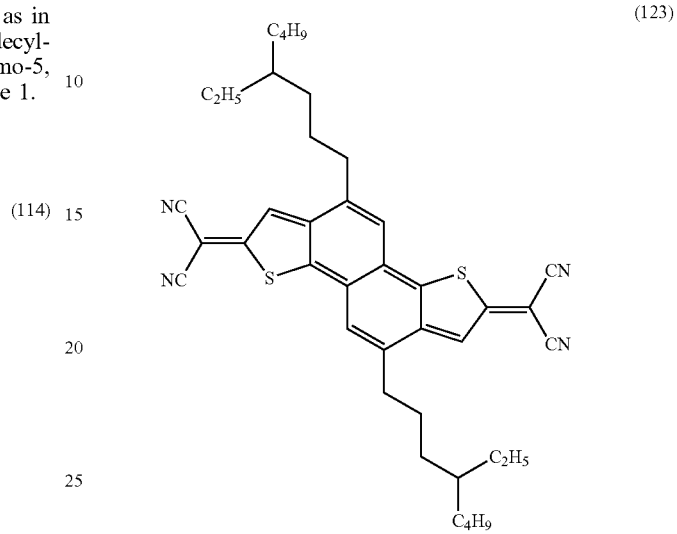

(123)

Compound 123 was obtained in a yield of 15%.
Measurement Result:
1H-NMR (400 MHz, CDCl$_3$) δ 0.91 (t, 6H), 0.95 (t, 6H), 1.24-1.42 (m, 16H), 1.71 (m, 2H), 2.71 (d, 4H) 7.05 (s, 2H), 7.57 (s, 2H)

Example 6

Compound 310 was obtained by the same process as in Example 1, except for using 2,7-dibromo-4,9-dioctylnaphtho[2,3-b:6,7-b']dithiophene in place of 2,7-dibromo-5,10-dioctylnaphtho[1,2-b:5,6-b']dithiophene in Example 1.

[Formula 27]

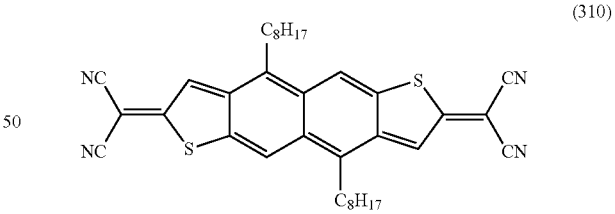

(310)

Compound 310 was obtained in a yield of 44%.
Measurement Result:
1H-NMR (400 MHz, CDCl$_3$) δ 0.89 (t, 6H), 1.24-1.42 (m, 20H), 1.67 (Quin, 4H), 2.99 (t, 4H) 7.50 (s, 2H), 7.52 (s, 2H)

Example 7

Compound 314 was obtained by the same process as in Example 1, except for using 2,7-dibromo-4,9-dihexadecyl-naphtho[2,3-b:6,7-b']dithiophene in place of 2,7-dibromo-5,10-dioctylnaphtho[1,2-b:5,6-b']dithiophene in Example 1.

[Formula 28]

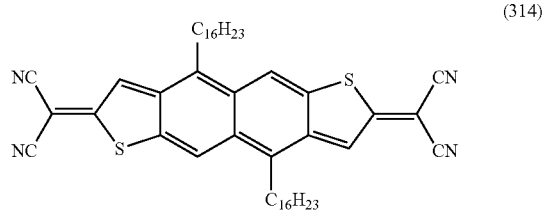

(314)

Compound 314 was obtained in a yield of 41%.
Measurement Result:
1H-NMR (400 MHz, CDCl$_3$) δ 0.89 (t, 6H), 1.24-1.42 (m, 52H), 1.67 (Quin, 4H), 2.99 (t, 4H) 7.50 (s, 2H), 7.52 (s, 2H)

Example 8

Compound 319 was obtained by the same process as in Example 1, except for using 2,7-dibromo-4,9-bis(2-ethylhexyl)naphtho[2,3-b:6,7-b']dithiophene in place of 2,7-dibromo-5,10-dioctylnaphtho[1,2-b:5,6-b']dithiophene in Example 1.

[Formula 29]

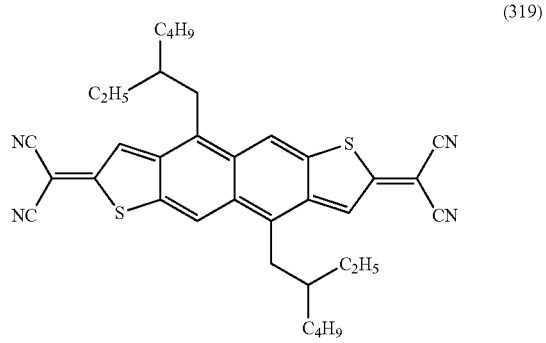

(319)

Compound 319 was obtained in a yield of 46%.
Measurement Result:
1H-NMR (400 MHz, CDCl$_3$) δ 0.89 (m, 12H), 1.24-1.42 (m, 16H), 1.67 (m, 2H), 2.99 (d, 4H) 7.50 (s, 2H), 7.52 (s, 2H)

Evaluation of physical properties of condensed polycyclic aromatic compounds
(1) Measurement of Solubility
Solubility was measured using chloroform as a solvent. Table 4 shows the mass percent concentrations of Compound 112 and Compound 119 when saturated chloroform solutions thereof were prepared.

TABLE 4

| | Solubility to Chloroform (w/w %) |
|---|---|
| Compound 112 | 0.20 |
| Compound 119 | 0.53 |

Figure 4:
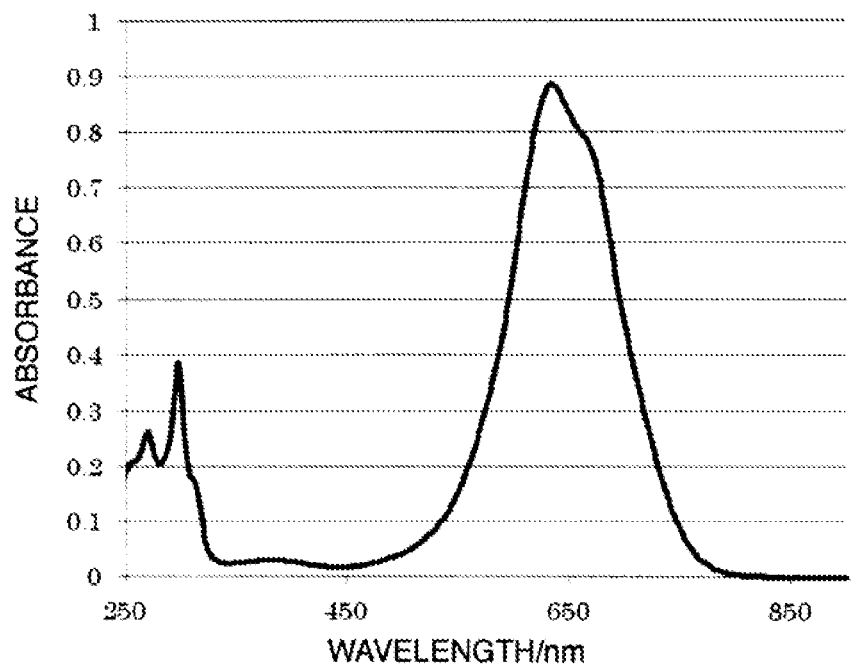
FIG. 4 is a graph showing a relation between the electron absorption spectrum and the absorption wavelength in the case of Compound 119 according to the present invention.

(2) Measurement of Electron Absorption spectrum (UV-Vis)
An electron absorption spectrum was measured using dichloromethane as a solvent. FIG. 4 shows a relation between the absorbance and the absorption wavelength λ (/nm) in the case of Compound 119. For Compounds 110, 112 and 114, similar spectra were observed.

Figure 5:
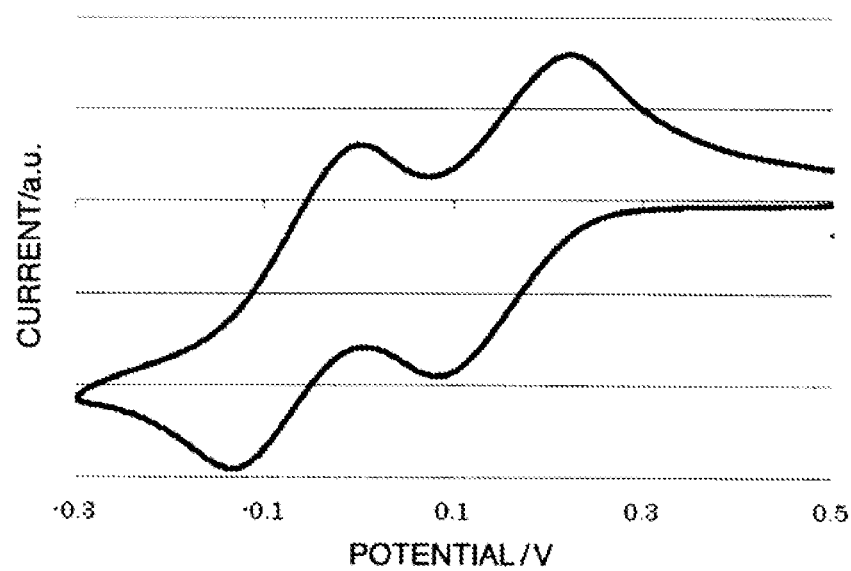
FIG. 5 is a graph showing a cyclic voltammogram of Compound 119 according to the present invention.

(3) Measurement of CV (Cyclic Voltammetry)
CV was measured using dichloromethane as a solvent, tetrabutylammonium hexafluorophosphate (n-BuN$_4$PF$_6$, 0.1 M) as a supporting salt, platinum wires as a working electrode and a counter electrode, and a silver/sliver chloride electrode as a reference electrode, and sweeping the electric potential at a rate of 100 mV/sec. FIG. 5 shows a relation between the current value and the potential (V) in the case of Compound 119. In all Compounds 110, 112, 114 and 119, two sets of oxidation-reduction waves were observed; the first half-wave reduction potentials were all 0.15 V in any, and the second half-wave reduction potentials were all −0.14 V. It was thus found that these compounds have high electron accepting ability.

(4) Evaluation of Transistor Properties
For evaluation of transistor properties of the above-described condensed polycyclic aromatic compounds, organic transistor devices were fabricated by the following process.

Organic thin films were formed on n-doped silicon wafers with a thermally oxidized-SiO$_2$ film using chloroform solutions of Compounds 110, 112, 114 and 119, by a spin coat process.

Then, Au was vacuum-deposited on the organic thin film using a shadow mask to thereby fabricate source/drain electrodes. The fabricated organic transistor device had a channel length of 50 μm, and a channel width of 1.5 mm. The organic transistor device is of a top-contact type; and FIG. 1B illustrates its structure.

It is to be noted that in the organic transistor devices of the Example, the thermally oxidized film on the n-doped silicon wafer functions as an insulator layer (4), and the n-doped silicon wafer functions as both a substrate (6) and a gate electrode (5).

The performance of an organic transistor device depends on the amount of current flowing when a potential is applied between a source and drain electrodes with a potential being applied on a gate electrode. The amount of current can be measured to determine the mobility, which is a characteristic of a transistor. The mobility can be calculated from the expression (a) representing an electric property of carrier species generated in an organic semiconductor layer as a result of application of a gate electric field on SiO$_2$ as an insulator.

$$Id = Z\mu Ci(Vg-Vt)2/2L \tag{a}$$

wherein, Id is a saturated source-drain current value; Z is a channel width; Ci is an electric capacity of an insulator; Vg is a gate potential; Vt is a threshold potential; L is a channel length; and μ is a mobility (cm$^2$/Vs) to be determined Ci is a dielectric constant of a SiO$_2$ insulator film used; Z and L are determined from the structure of an organic transistor device; Id and Vg are determined when the current value of an organic transistor device is measured; and Vt can be determined from Id and Vg. By substituting each value for the expression (a), corresponding mobilities at gate potentials can be calculated.

Transistor properties of the above-described condensed polycyclic aromatic compounds, i.e. Compounds 110, 112, 114, 119 and 319, were evaluated in the air atmosphere. Table 5 shows the results of the transistor properties.

TABLE 5

| | Mobility (cm$^2$V$^{-1}$s$^{-1}$) | On/Off Ratio | Threshold Potential (V) |
|---|---|---|---|
| Compound 110 | 3.3 × 10$^{-2}$ | 10$^3$ | 8.5 |
| Compound 112 | 4.8 × 10$^{-2}$ | 10$^3$ | 3.3 |
| Compound 114 | 3.3 × 10$^{-2}$ | 10$^4$ | 1.4 |
| Compound 119 | 0.12 | 10$^4$ | 2.3 |
| Compound 319 | 6.8 × 10$^{-3}$ | 10$^3$ | 1.4 |

Industrial Applicability

As described hitherto, the present invention, since being able to improve the solubility, the conductivity and the electron mobility of the condensed polycyclic aromatic compound and the organic semiconductor material, is enabled to provide the condensed polycyclic aromatic compound and the organic semiconductor material allowing the utilization of a solution process and allowing the stable n-type transistor operation even in the air atmosphere. Hence, the present invention is enabled to be utilized in the fields such as organic transistor devices, diodes, capacitors, thin film photoelectric conversion devices, dye-sensitized solar cells, organic EL devices and the like.

Reference Signs List

In FIG. 1 to FIG. 3, the same reference number is attached to the same designation.
1 SOURCE ELECTRODE
2 SEMICONDUCTOR LAYER
3 DRAIN ELECTRODE
4 INSULATOR LAYER
5 GATE ELECTRODE
6 SUBSTRATE
7 PROTECTION LAYER

The invention claimed is:

1. A condensed polycyclic aromatic compound represented by general formula (1):

[Formula 1]

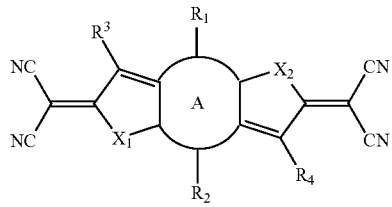

(1)

wherein A represents a 1,5-dihydronaphthalene ring or a 2,6-dihydronaphthalene ring; $R_1$, $R_2$, $R_3$ and $R_4$ each independently represent a hydrogen atom, a halogen atom, a substituted or unsubstituted aliphatic hydrocarbon group, a substituted or unsubstituted alicyclic hydrocarbon group, a substituted or unsubstituted aromatic hydrocarbon group, a substituted or unsubstituted hydrocarbon oxy group, a substituted or unsubstituted ester group, a substituted or unsubstituted acyl group or a substituted or unsubstituted cyano group; and $X_1$ and $X_2$ each independently represent an oxygen atom, a sulfur atom or a selenium atom.

2. The condensed polycyclic aromatic compound according to claim 1, wherein $X_1$ and $X_2$ are sulfur atoms.

3. The condensed polycyclic aromatic compound according to claim 1, wherein $R_3$ and $R_4$ are hydrogen atoms.

4. The condensed polycyclic aromatic compound according to claim 1, wherein $R_1$ and $R_2$ are each an aliphatic hydrocarbon group having 1 to 30 carbon atoms.

5. The condensed polycyclic aromatic compound according to claim 4, wherein $R_1$ and $R_2$ are each a straight-chain or branched-chain alkyl group having 1 to 30 carbon atoms.

6. An organic semiconductor material comprising the condensed polycyclic aromatic compound according to any one of claims 1 to 5.

7. The organic semiconductor material according to claim 6, wherein the organic semiconductor material is a transistor material.

8. A composition for forming a thin film comprising the condensed polycyclic aromatic compound according to any one of claims 1 to 5, and an organic solvent.

9. The composition for forming a thin film according to claim 8, wherein the content of the condensed polycyclic aromatic compound is in the range of 0.01 part by weight or higher and 10 parts by weight or lower relative to 100 parts by weight of the organic solvent.

10. A thin film comprising the condensed polycyclic aromatic compound according to any one of claims 1 to 5.

11. An organic semiconductor device comprising the thin film according to claim 10.

12. The organic semiconductor device according to claim 11, wherein the device is an organic transistor device.

13. A method for producing an organic semiconductor device, comprising a step of applying the composition for forming a thin film according to claim 8 onto a substrate by a solution process.

14. A method for producing an organic semiconductor device, comprising a step of applying the composition for forming a thin film according to claim 9 onto a substrate by a solution process.

* * * * *